US010436726B2

(12) United States Patent
Lei et al.

(10) Patent No.: US 10,436,726 B2
(45) Date of Patent: Oct. 8, 2019

(54) PALM-SIZE μNMR RELAXOMETER USING A DIGITAL MICROFLUIDIC (DMF) DEVICE AND A SEMICONDUCTOR TRANSCEIVER FOR CHEMICAL/BIOLOGICAL DIAGNOSIS

(71) Applicant: UNIVERSITY OF MACAU, Taipa, Macau (CN)

(72) Inventors: Ka-Meng Lei, Macau (CN); Pui-In Mak, Macau (CN); Man-Kay Law, Macau (CN); Rui Paulo Da Silva Martins, Macau (CN)

(73) Assignee: UNIVERSITY OF MACAU, Taipa, Macau (CN)

( * ) Notice: Subject to any disclaimer, the term of this patent is extended or adjusted under 35 U.S.C. 154(b) by 726 days.

(21) Appl. No.: 14/881,889

(22) Filed: Oct. 13, 2015

(65) Prior Publication Data

US 2017/0102344 A1   Apr. 13, 2017

(51) Int. Cl.
| | |
|---|---|
| *G01N 24/08* | (2006.01) |
| *G01R 33/44* | (2006.01) |
| *G01R 33/30* | (2006.01) |
| *G01R 33/341* | (2006.01) |
| *G01R 33/34* | (2006.01) |
| *G01R 33/36* | (2006.01) |

(52) U.S. Cl.
CPC ............ *G01N 24/08* (2013.01); *G01R 33/302* (2013.01); *G01R 33/341* (2013.01); *G01R 33/448* (2013.01); *G01R 33/34007* (2013.01); *G01R 33/3607* (2013.01); *G01R 33/3621* (2013.01)

(58) Field of Classification Search
None
See application file for complete search history.

(56) References Cited

U.S. PATENT DOCUMENTS

| | | | | |
|---|---|---|---|---|
| 2006/0186951 | A1* | 8/2006 | Ohannaidh | ........ H03H 11/1213 327/552 |
| 2007/0016003 | A1* | 1/2007 | Piron | ................... A61B 5/415 600/415 |
| 2011/0091987 | A1* | 4/2011 | Weissleder | ........... G01R 33/302 436/173 |

OTHER PUBLICATIONS

C. D. Chin, V. Linder and S. K. Sia,"Lab-on-a-chip devices for global health: Pat studies and future opportunities", *Lab Chip*, 2007, 7, 41-57.

(Continued)

*Primary Examiner* — Jermele M Hollington
*Assistant Examiner* — Suresh K Rajaputra
(74) *Attorney, Agent, or Firm* — Ladas & Parry LLP

(57) ABSTRACT

A palm-size portable μNMR relaxometer system for performing multi-step multi-sample chemical/biological assays, comprising a PCB having a CMOS μNMR transceiver and a DMF device integrated thereon. A portable magnet has an inner gap configured to at least partially receive the DMF device. The DMF device comprises a platform of electrodes including a sensing site and receives one or more samples for analysis at an electrode and automatically transports the one or more samples on individual paths sequentially to the sensing site, for performing sensing on each sample sequentially. A Butterfly coil disposed on the PCB and underneath the DMF device and is at least partially received in the inner gap. The Butterfly coil excites the sample at the μNMR sensing site by transducing a magnetic field produced at the sensing site to an electrical signal which is processed by the CMOS μNMR transceiver to produce an analytical signal.

25 Claims, 13 Drawing Sheets

(56) References Cited

OTHER PUBLICATIONS

P. Yager, G. J. Domingo and J. Gerdes, "Point-of-Care Diagnostics for Global Health", Annu. Rev. Biomed Eng., 2008, 10, 107-144.
D. A. Giljohann and C. A. Mirkin, "Drivers of biodiagnostic development", Nature, 2009, 462, 461-464.
D. G. Storla, S. Yimer and G. A. Bjune, "A systemic review of delay in the diagnosis and treatment of tuberculosis", BMC Pub. Health, 2008, 8, 15-23.
E. W. M. Kemna, L. I. Segerink, F. Wolbers, I. Vermes and A. Berg, "Label-free, high-throughput, electrical detection of cells in droplets", Analyst, 2013, 138, 4585-4292.
J. O. Esteves-Villanueva, H. Trzeciakiewicz and S. Martic , "A protein-based electrochemical biosensor for detection of tau protein, a neurodegenerative disease biomarker", Analyst, 2014, 139, 2823-2831.
P. Liu, K. Skucha, M. Megens and B. Boser, "A CMOS Hall-Effect Sensor for the Characterization and Detection of Magnetic Nanoparticles for Biomedical Applications", IEEE Trans. Magn., 2011, 47(10), 3449-3451.
A. Pai, A. Khachaturian, S. Chapman, A. Hu, H. Wang and A. Hajimiri, "A handheld magnetic sensing platform for antigen and nucleic acid detection", Analyst, 2014, 139, 1403-1411.
M. Safavieh, M. U. Ahmed, E. Sokullu, A. Ng, L. Braescu and M. Zourob, "A simple cassette as point-of-care diagnostic device for naked-eye colorimetric bacteria detection", Analyst, 2014, 139, 482-487.
E. Wajs, F. Caldera, F. Trotta and A. Fragoso, "Peroxidase-encapsulated cyclodextrin nanosponge immunoconjugates as a signal enhancement tool in optical and electrochemical assays", Analyst, 2014, 139, 375-380.
L. Josephson, J. M. Perez and R. Weissleder, "Magnetic Nanosensors for the Detection of Oligonucleotide Sequences", Angew. Chem., Int. Ed, 2001, 113(17), 3304-3306.
J. M. Perez, L. Josephson, T. O'Loughlin, D. Högemann and R. Weisselder, "Magnetic relaxation switches capable of sensing molecular interactions", Nat. Biotechnol., 2002, 20, 816-820.
H. Lee, E. Sun, D. Ham and R. Weissleder, "Chip-NMR biosensor for detection and molecularanalysis of cells", Nat. Med., 2008, 14(8), 869-874.
M. Liong, A. N. Hoang, J. Chung, N. Gural, C. B. Ford, C. Min, R. R. Shah, R. Ahmad, M. Fernandez-Suarez, S. M. Fortune, M. Toner, H. Lee and R. Weissleder, "Magnetic barcode assay for genetic detection of pathogens", Nat. Commun., 2013, 4(1752), 1-9.
N. Sun, T-J. Yoon, H. Lee, W. Andress, R. Weissleder and D. Ham, "Palm NMR and 1-Chip NMR", IEEE J. Solid-State Circuits, 2011, 46(1), 342-352.
N. Sun, Y. Liu, H. Lee, R. Weissleder and D. Ham, "CMOS RF Biosensor Utilizing Nuclear Magnetic Resonance", IEEE J. Solid-State Circuits, 2009, 44(5), 1629-1643.
D. Ha, J. Paulsen, N. Sun, Y.-Q. Song and D. Ham, "Scalable NMR spectroscopy with semiconductor chips", Proc. Nat. Acad. Sci., 2014, 111(13), 11955-11960.
J. D. Trumbull, I. K. Glasgow, D. J. Beebe and R. L. Magin, "Integrating Microfabricated Fluidic Systems and NMR Spectroscopy", IEEE Trans. Biomed. Eng., 2000, 47(1), 3-7.
C. Massin, F. Vincent, A. Homsy, K. Ehrmann, G. Boero, P.-A. Besse, A. Daridon, E. Verpoorte, N. F. de Rooij and R. S. Popovica, "Planar microcoil-based microfluidic NMR probes", J. Magn. Reson., 2003, 164(2), 242-255.
A. R. Wheeler, "Putting Electrowetting to Work", Science, 2008, 322, 539-540.
J. Gao, X. Liu, T. Chen, P.-I. Mak, Y. Du, M.-I. Vai, B. Lin and R. P. Martins, "An intelligent digital microfluidic system with fuzzy-enhanced feedback for multi-droplet manipulation", Lab Chip, 2013, 13, 443-451.
M. H. Shamsi, K. Choi, A. H. C. Ng and A. R. Wheeler, "A digital microfluidic electrochemical immunoassay", Lab Chip, 2014, 14, 547-554.
F. Lapierre, M. Harnois, Y. Coffinier, R. Boukherroub and V. Thomy, "Split and flow: reconfigurable capillary connection for digital microfluidic devices", Lab Chip, 2014, 14, 3589-3593.
I. Barbulovic-Nad, H. Yang, P. S. Park and A. R. Wheeler, "Digital microfluidics for cell-based assays", Lab Chip, 2008, 8, 519-526.
G. J. Shah, A. T. Ohta, E. P.-Y. Chiou, M. C. Wu and C. J. Kim, "EWOD-driven droplet microfluidic device integrated with optoelectronic tweezers as an automated platform for cellular isolation and analysis", Lab Chip, 2009, 9, 1732-1739.
I. Barbulovic-Nad, S. H. Au and A. R. Wheeler, "A microfluidic platform for complete mammalian cell culture", Lab Chip, 2010, 10, 1536-1542.
Y. H. Chang, G. B. Lee, F. C. Huang, Y. Y. Chen and J. L. Lin, "Integrated polymerase chain reaction chips utilizing digital microfluidics", Biomed Microdevices, 2006, 8, 215-225.
R. Sista, Z. Hua, P. Thwar, A. Sudarsan, V. Srinivasan, A. Eckhardt, M. Pollack and V. Pamula, "Development of a digital microfluidic platform for point of care testing", Lab Chip, 2008, 8, 2091-2104.
Z. Hua, J. L. Rouse, A. E. Eckhardt, V. Srinivasan, V. K. Pamula, W. A. Schell, J. L. Benton, T. G. Mitchell and M. G. Pollack, "Multiplexed Real-Time Polymerase Chain Reaction on a Digital Microfluidic Platform", Anal. Chem. 2010, 82(6), 2310-2316.
D. Witters, K. Knez, R. Ceyssens, R. Puers and J. Lammertyn, "Digital microfluidics-enabled single-molecule detection by printing and sealing single magnetic beads in femtoliter droplets", Lab Chip, 2013, 13, 2047-2054.
K.-M. Lei, P.-I. Mak, M.-K. Law, R. P. Martins, "NMR-DMF: a modular nuclear magnetic resonance-digital microfluidics system for biological assays", Analyst, DOI: 10.1039/c4an01285b, 2014, 6204-6313.
M. Muluneh and D. Issadore, "Microchip-based detection of magnetically labeled cancer biomarkers", Adv. Drug Deliv. Rev., 2014, 66, 101-109.
D. Issadore, C. Min, M. Liong, J. Chung, R. Weissleder and H. Lee, "Miniature magnetic resonance system for point-of-care diagnostics", Lab Chip, 2011, 11, 2282-2287.
C. Dong, T. L. Chen, J. Gao. Y. W. Jia. P.-I. Mak, M.-I. Vai and R. P. Martins, "On the droplet velocity and electrode lifetime of digital microfluidics: voltage actuation techniques and comparison",Microfluid. Nanofluid., DOI 10.1007/s10404-014-1467-y, 2014, 673-683.
A. Rival, D. Jary, C. Delattre, Y. Fouillet, G. Castellan, A. Bellemin-Comte and X. Gidrol, "An EWOD-based microfluidic chip for single-cell isolation, mRNA purification and subsequent multiplex qPCR", Lab Chip, 2014, 14, 3739-3749.
P. Y. Keng, S. Chen, H. Ding, S. Sadeghi, G. J. Shah, A. Dooraghi, M. E. Phelps, N. Satyamurthy, A. F. Chatziioannou, C. J. Kim and R. M. van Dam, "Micro-chemical synthesis of molecular probes on an electronic microfluidic device", Proc. Nat. Acad. Sci., 2012, 109(3), 690-695.
L. Indrawati, R. L. Stroshine and G. Narsimhan, "Low-field NMR: A tool for studying protein aggregation", J. Sci. Food Agric., 2007, 87(12), 2207-2216.
L. Luan, R. D. Evans, N. M. Jokerst, R. B. Fair, "Integrated Optical Sensor in a Digital Microfluidic Platform", IEEE Sens. J., 2008, 8(5), 628-635.
S. C. C. Shih, I. Barbulovic-Nad, X. Yang, R. Fobel, A. R. Wheeler, "Digital microfluidics with impedance sensing for integrated cell culture and analysis", Biosens. Bioelectron., 2013, 42, 314-320.
S. D'Amico, M. Conta, and A. Baschirotto, "A 4.1-mW 10-MHz Fourth-Order Source-Follower-Based Continuous-Time Filter with 79-dB DR", IEEE J of Solid State Circuits, 2006, 41(12), 2713-2719.

\* cited by examiner

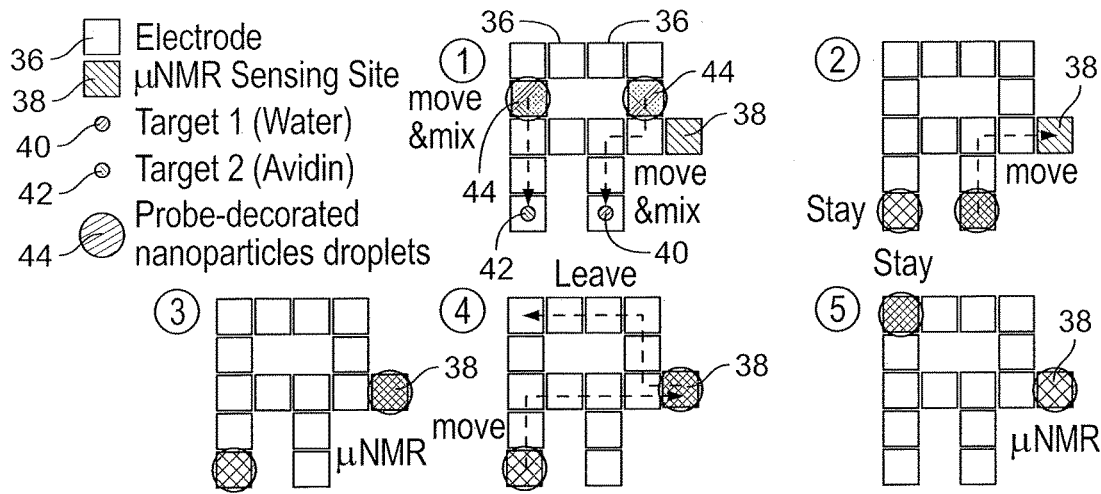
FIG. 7(a)
| Droplet No.1 | Move to the target | Move the μNMR sensing site | Perform μNMR | Leave | Stay |
|---|---|---|---|---|---|
| | 4 Steps, 12 s | 4 Steps, 12 s | Repeat 8x, 48 s in total | 6 Steps, 18 s | 43 s |
| Droplet No.2 | Move to the target | Stay | Move the μNMR sensing site | Perform μNMR |
|---|---|---|---|---|
| | 3 Steps, 9 s | 58 s | 6 Steps, 18 s | Repeat 8x, 48 s in total |
FIG. 7(b)
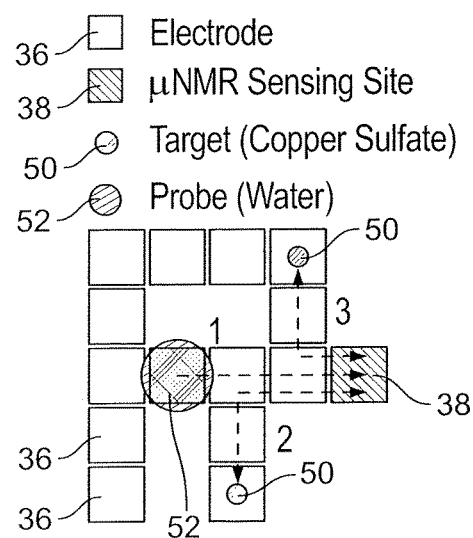
FIG. 8(a)
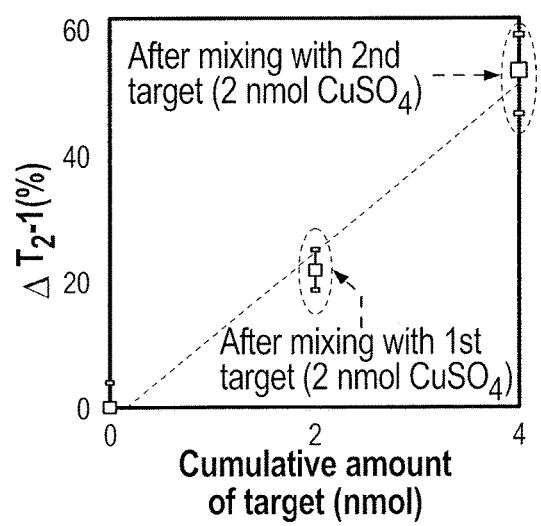
FIG. 8(b)

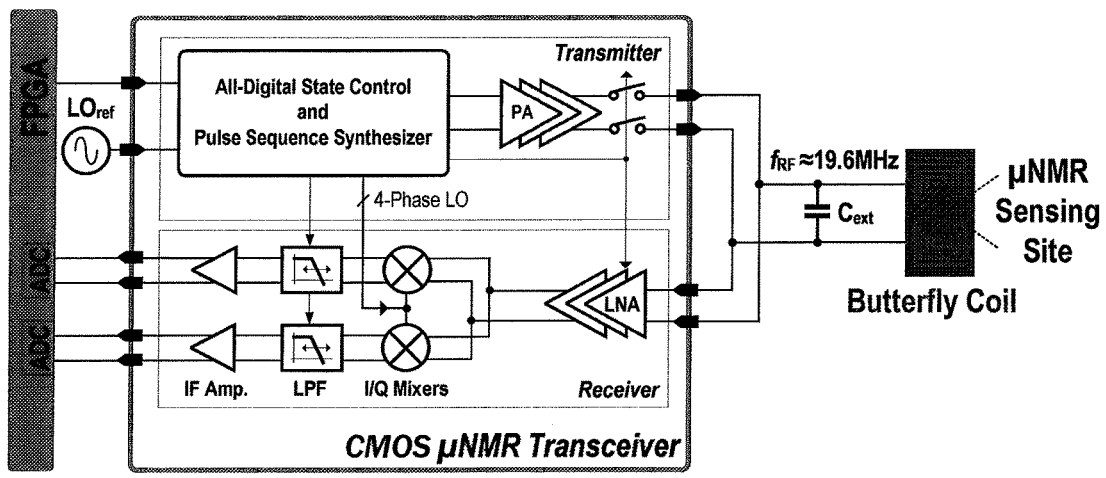
FIG. 11
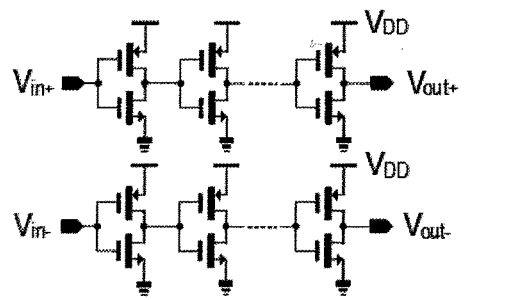
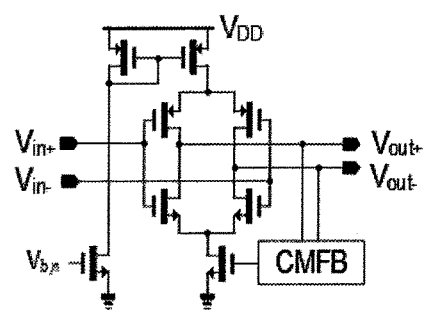
Fig. 12(a)   Fig. 12(b)
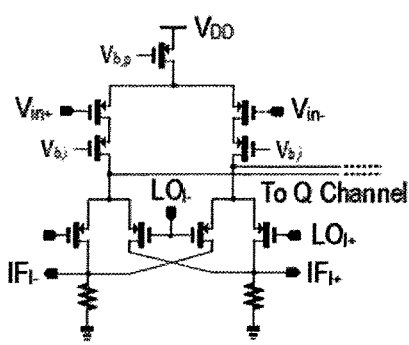
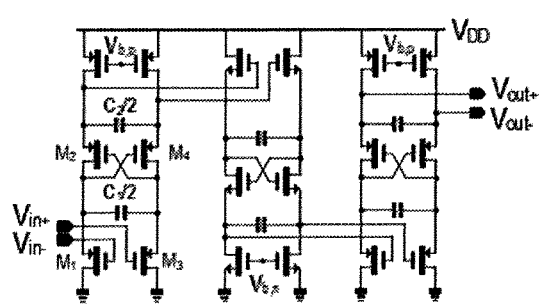
Fig. 12(c)   Fig. 12(d)

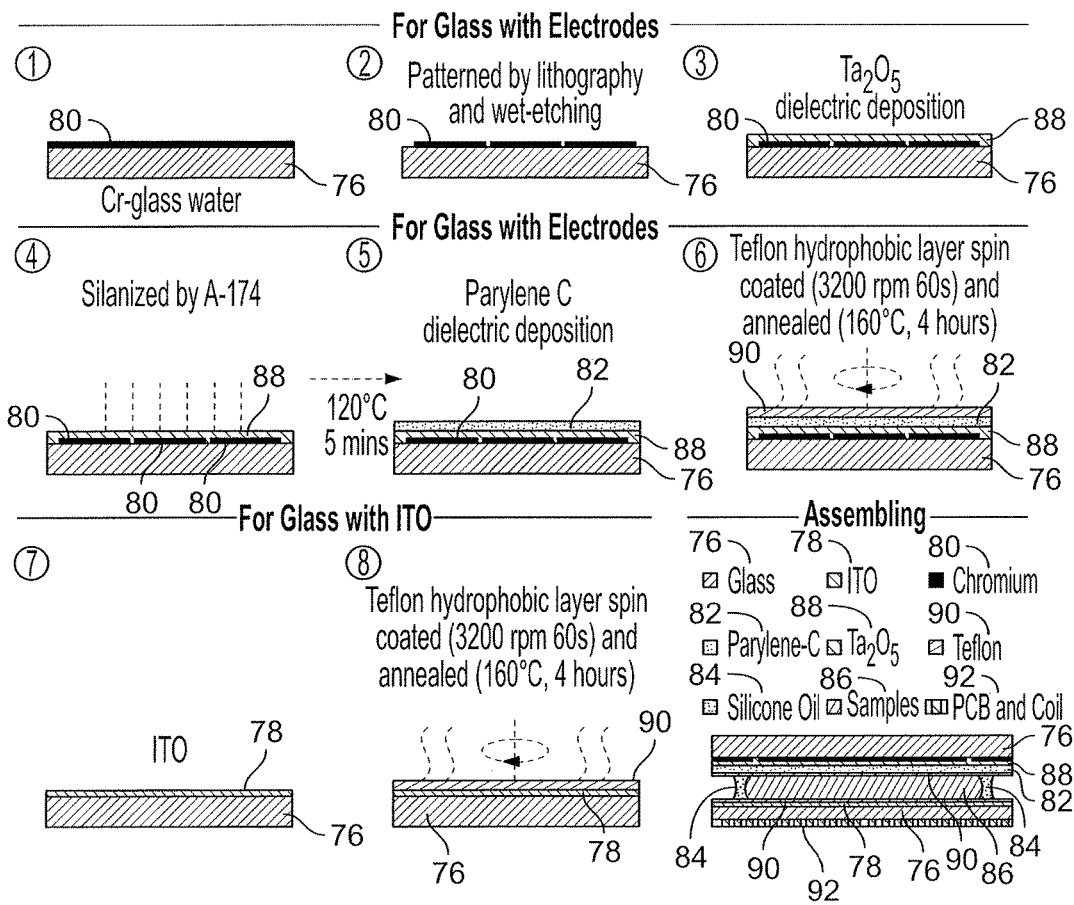
FIG. 19
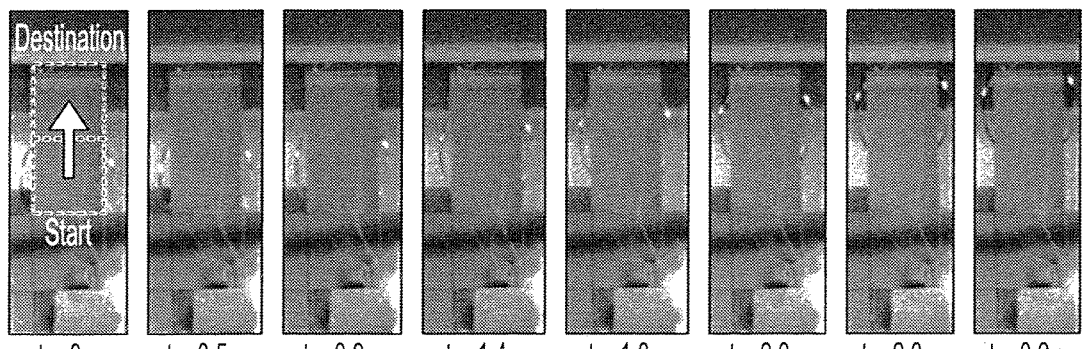
FIG. 20(a)   FIG. 20(c)   FIG. 20(e)   FIG. 20(g)
FIG. 20(b)   FIG. 20(d)   FIG. 20(f)   FIG. 20(h)

Table 1 Comparison of the systematic specification and the functionality of recent μNMR systems.

| | N. Sun et al. 2009 & 2011 | D. Ha et al. 2014 | K.-M. Lei et al. 2014 | This Work |
|---|---|---|---|---|
| NMR type | Relaxometry | Spectroscopy | Relaxometry | Relaxometry |
| Coil type | Off-/on-chip Spiral | Off-chip Solenoid | Off-chip PCB Butterfly | Off-chip PCB Butterfly |
| Magnet (B-field, weight and size) | 0.5 T, 1.2 kg, Ø 8cm x H 5cm | 0.51 T, 7.3 kg, Ø 11.8cm x H 12.6cm | 0.5 T, 1.2 kg, Ø 8cm x H 5cm | 0.5 T, 1.2 kg, Ø 8cm x H 5cm |
| Sample management | Manual (direct on coil) | Manual (capillary injection) | Limited (without feedback and timing) | Automatic (real-time feedback) |
| Sample per experiment | Single | Single | Single | At least 2 distinct samples |
| Pre/Post-sample reaction supportability | No | No | Restricted (due to limited electrodes) | Flexible (e.g., merge, separate, translate) |
| Calibration of magnetic field fluctuation | No | Offline (by software) | No | Online (by hardware) |

Fig. 22

PALM-SIZE μNMR RELAXOMETER USING A DIGITAL MICROFLUIDIC (DMF) DEVICE AND A SEMICONDUCTOR TRANSCEIVER FOR CHEMICAL/BIOLOGICAL DIAGNOSIS

BACKGROUND OF THE INVENTION

Field of the Invention

The present invention generally relates to a system, apparatus, method, and program serving as a palm-size electronic-automated micro-nuclear magnetic resonance (μNMR) relaxometer integrated with a Digital Microfluidic (DMF) device and an optimized Butterfly-coil-input CMOS transceiver to extend capability and enhance performance for chemical and/or biological diagnosis.

Related Art

With lab-on-a-chip devices there is a desire to miniaturize benchtop laboratory apparatuses into handheld tools for point-of-care (POC) diagnosis, while featuring orders-of-magnitude reduction of hardware cost and sample use. This vision implies tantalizing advantages over the laboratory tests, especially for rapid pre-screening of infectious diseases such as, e.g., human immune-deficiency virus, tuberculosis, and Ebola, particularly in under-developed worlds.

The inventors of the present application note that although a wide variety of POC diagnostic tools have been reported, such as those utilizing electrical sensing, magnetic sensing, or optical detection, none of them has explored the prospects of micro-nuclear magnet resonance (μNMR) with the advanced microfluidic and microelectronic technologies.

SUMMARY OF THE INVENTION

General NMR systems have been proven to be a fairly reliable tool for diagnosis of a wide range of biological targets, such as Oligonucleotides, proteins, *Mycobacterium Tuberculosis*, and cancer cells, specifically due to the pre-designed probe-decorated nanoparticles (NP). Existence of the targets will capture the probe-decorated NP hence altering the spin-spin relaxation time ($T_2$) of the samples. Also, initiated by the sensitivity improvement of complementary metal-oxide-semiconductor (CMOS) μNMR transceiver chips, a number of recent works have been focusing on miniaturizing the weight and size of NMR systems. With a moderate magnetic field (<1 T) handheld magnet (weight <7.3 kg), it was possible to demonstrate the detection of biological targets and the observation of molecule structures to achieve a POC diagnosis platform where a high magnetic field is nonessential.

The inventors of the present application note that regrettably, restrained by the limited inner volume of a high-homogeneity handheld magnet, the sample management poses a substantial barrier for μNMR systems. As the opening gap of the magnet can be only 32 mm×14 mm, sample placement and mixing of probe-decorated NP with samples under analysis have to be manually pre-treated outside the magnet. Confounded by these operations which heavily rely on human efforts, the reproducibility of the results and throughput are deteriorated while raising the chance of sample contamination. Despite several works that have managed to surmount sample manipulation for NMR including capillary electrophoresis and microfluidic channels, they still failed to avoid non-integrated laboratory gadgets, e.g., micro-pumps and valves.

Unlike conventional channel microfluidics, digital microfluidics (DMF) is highly amenable to integration, electronic automation, and re-configuration. DMF is also bio-compatible and has been adopted in a wide variety of applications including cell culturing, DNA amplification, and single protein molecule capturing. Microdroplets (e.g., <10 μL) in the DMF device can be transported over an electrode array by modifying the surface tension of the electrode utilizing the principle of electrowetting-on-dielectric (EWOD). The inventors note that such distinct microdroplet controllability renders the DMF a promising droplet management platform for POC devices, especially for integration with μNMR. However, confounded by the unintegrated DMF device and discrete electronics, only manual droplet operation with one sample and one target was demonstrated, while lacking of position feedback to master the route of the droplets and temperature tracking to compensate the magnetic field variation.

The present invention in one example embodiment discloses the first palm-size electronic-automated μNMR relaxometer integrated with a DMF device/electronics and an optimized Butterfly-coil-input CMOS transceiver to extend capability and enhance performance. The former allows multiple-sample management in real-time with position feedback for flexible and automatic droplet manipulation and reaction, attaining a close-loop control for the system to master the entire operation of the droplets efficiently. The latter is enabled by analog circuitry techniques together with cross-domain design and modelling to culminate in low-power high-sensitivity μNMR screening within the limited inner volume of the magnet. It features in one example embodiment an approximately 1000× electronics volume shrinkage with an integrated low-pass filter compared to the modular counterpart.

Development of μNMR systems over the past decade is depicted in FIG. 10, and some differences of the present invention with the functionality of recent μNMR systems are shown in Table 1 presented in FIG. 22 wherein "This Work" as labeled in FIG. 10 is directed to the present invention (see also the further discussion in the Electronic Supplementary Information section or ESI below).

In the present invention the μNMR relaxometer is integrated with a DMF device to support multi-step multi-sample diagnosis in a portable platform. The entire DMF protocol involves software control as well as hardware actuation and sensing to master the operation of the droplets. This integration of distinct technologies enables multiple and simultaneous chemical/biological diagnosis in a unified experiment or system that is crucial for bio-assays. Additionally, as the DMF device is integrated with the μNMR model onto the same printed circuit board (PCB) substrate, the suppressed variation of droplet position culminates in high reproducibility of the diagnostic results. Finally, a temperature-tracking local oscillator ($LO_{ref}$) is also adopted to enhance the robustness of the μNMR relaxometer over a wide range of ambient temperature (0 to 40° C.). This scheme is more advantageous and befitting to a rapid and portable diagnostic tool as this refrains from sweeping over a wide range of $LO_{ref}$ frequency or entailing massive computation, which are time and power consuming. This multidisciplinary platform can provide a solution for the POC diagnosis system.

The present invention in one aspect provides a portable μNMR relaxometer system for performing multi-step multi-sample chemical/biological assays. The system comprises a printed circuit board (PCB) having a CMOS μNMR transceiver and a Digital Microfluidic (DMF) device integrated thereon. The system also comprises a portable magnet generating a static magnetic field and having an inner gap that is configured to at least partially receive the DMF device. The DMF device comprises a platform of electrodes using electro-wetting-on-dielectric (EWOD) effects, the platform including a sensing site and having top and bottom planes for squeezing a sample. The DMF device is configured to receive one or more samples for analysis at an electrode on the platform and automatically transport the one or more samples on individual paths sequentially to the sensing site, for performing sensing on each sample sequentially. The CMOS μNMR transceiver comprises an μNMR circuit that interfaces with a Butterfly coil. The Butterfly coil is disposed on the PCB and directly underneath the DMF device and is at least partially received in the inner gap of the portable magnet. The Butterfly coil generates a surface-parallel RF magnetic field orthogonal to the static magnetic field generated by the portable magnet for exciting the sample at the μNMR sensing site by transducing a magnetic field produced at the sensing site to an electrical signal which is processed by the CMOS μNMR transceiver to produce an analytical signal.

The present invention in another aspect provides a method for performing multi-step multi-sample chemical/biological assays using a portable μNMR relaxometer system which comprises a printed circuit board (PCB) having a CMOS μNMR transceiver and a Digital Microfluidic (DMF) device integrated thereon, and a portable magnet generating a static magnetic field and having an inner gap that is configured to at least partially receive the DMF device, wherein the DMF device comprises a platform of electrodes using electro-wetting-on-dielectric (EWOD) effects, the platform including a sensing site and having top and bottom planes for squeezing a sample. The method comprises receiving one or more samples for analysis at an electrode on the platform, and automatically transporting the one or more samples on individual paths of the platform sequentially to the sensing site, for performing sensing on each sample sequentially. The method also comprises interfacing with a Butterfly coil disposed on the PCB and directly underneath the DMF device and being at least partially received in the inner gap of the portable magnet, the Butterfly coil generating a surface-parallel RF magnetic field orthogonal to the static magnetic field generated by the portable magnet for exciting the sample at the μNMR sensing site by transducing a magnetic field produced at the sensing site to an electrical signal. The method further comprises processing the electrical signal by the CMOS μNMR transceiver to produce an analytical signal.

The present invention in another aspect provides a non-transitory computer-readable medium storing a program which, when executed by at least one processor, performs a method for performing multi-step multi-sample chemical/biological assays using a portable μNMR relaxometer system which comprises a printed circuit board (PCB) having a CMOS μNMR transceiver and a Digital Microfluidic (DMF) device integrated thereon, and a portable magnet generating a static magnetic field and having an inner gap that is configured to at least partially receive the DMF device, wherein the DMF device comprises a platform of electrodes using electro-wetting-on-dielectric (EWOD) effects, the platform including a sensing site and having top and bottom planes for squeezing a sample. The method comprises controlling the DMF device to automatically transport one or more samples received at an electrode on the platform, on individual paths of the platform sequentially to the sensing site, for performing sensing on each sample sequentially.

Further features and advantages of the present invention as well as the structure and operation of various embodiments of the present invention are described in detail below with reference to the accompanying drawings.

BRIEF DESCRIPTION OF THE DRAWINGS

The features and advantages of the present invention will be more readily understood from a detailed description of the exemplary embodiments taken in conjunction with the following figures.

FIG. 7(a) is an illustration of the motions of the droplets for multi-step multi-sample handling. Two identical probe-decorated NP droplets 44 are placed inside the DMF device 14 together with two targets 40, 42 (water 40 as control, and avidin 42). The probe-decorated NP droplets 44 are then gradually transported to the target site for mixing with the respective target. After mixing, one of the mixture is transported to the μNMR sensing site 38 while the other stays on its electrode. Upon the first mixture finishing the μNMR analysis, the first mixture is guided away from the μNMR sensing site 38 and the second mixture comes in. These operations demonstrate that the μNMR relaxometer 10 can handle and perform multi-step and multi-sample μNMR analysis. ($T_2$ of water sample: 256 ms; avidin: 211 ms)

FIG. 7(b) shows a Gantt chart of the operation of an individual droplet. With software control in the computer, the route of the droplets and the protocols can be optimized and the duration of the experiment can be minimized. The turnaround time for the experiment is, in this example embodiment, approximately 2.2 minutes.

FIG. 8(a) is an illustration of one multi-step experiment. The probe (water alone) 52 is firstly guided to the NMR sensing site 38 for recording the spin-spin relaxation time as a reference. Then the probe 52 is mixed with the 1st target 50 and the mixture is transported to the NMR sensing site 38 for concentration identification. Subsequently the droplet 52 is mixed with the 2nd target 50 and the resultant droplet is driven to the NMR sensing site 38 again for quantification. The sequence of the droplet operations are marked on the figure.

FIG. 8(b) illustrates a variation of $T_2$ upon reaction with the $CuSO_4$ ions. The $T_2$ of the droplet is changed upon mixing with the $CuSO_4$ ions, which reveals the capability of the relaxometer 10 to perform a multi-step NMR experiment.

FIG. 11 is a schematic of an μNMR transceiver 17 and its connection to the external parts including a Butterfly coil 18 according to an example embodiment of the present invention.

FIG. 12, comprising FIGS. 12(a)-(d), are schematics of key functional blocks according to an example embodiment of the present invention: FIG. 12(a) shows a power-efficient multi-stage inverter-based PA 58; FIG. 12(b) shows an NMOS-PMOS differential-pair LNA 60 with high gain and low noise; FIG. 12(c) shows I/Q active mixers 62 with a common PMOS differential pair for noise reduction; and FIG. 12(d) shows area-efficient and high-linearity 6th-order source-follower-based LPF 64.

FIG. 19 shows a fabrication procedure of a $Ta_2O_5$/Parylene C-insulated DMF device 14 according to an embodiment of the present invention. Steps 1 to 6 show the fabrication process of the plate with electrode, while the fabrication process of the plate with ITO is shown in step 7 to 8. The assembly of the DMF device 14 together with the Butterfly coil 18 is also shown in the figure.

FIGS. 20(a)-(h) are snapshots of the DMF device 14 transporting the droplets from t=0 s to t=3.2 s. At t=0 s, the square wave was applied to the neighboring electrode, causing the surface tension of the droplet near the electrode to change and attract the droplet.

FIG. 22 presents Table 1, which shows a comparison of some of the systematic specifications of the present invention with the functionality of recent μNMR systems.

The invention will next be described in connection with certain exemplary embodiments; however, it should be clear to those skilled in the art that various modifications, additions, and subtractions can be made without departing from the spirit or scope of the claims.

DETAILED DESCRIPTION OF THE PREFERRED EMBODIMENTS

1. Overview

The present invention according to one aspect discloses a micro-nuclear magnetic resonance (μNMR) relaxometer miniaturized into palm-size, and electronic-automated for multi-step multi-sample chemical/biological diagnosis. The integration of microfluidic and microelectronic technologies disclosed herein enables association between droplet management and μNMR assays inside a portable sub-Tesla magnet (e.g., 1.2 kg, 0.46 Tesla in one example embodiment). Targets in unprocessed biological samples, captured by specific probe-decorated magnetic nanoparticles (NP), can be sequentially quantified by their spin-spin relaxation time (T2) via multiplexed μNMR screening. Distinct droplet samples are operated by a digital microfluidic (DMF) device that electronically manages the electrowetting-on-dielectric (EWOD) effects over an electrode array. Each electrode (e.g., 3.5×3.5 mm$^2$ in an example embodiment) is scanned with capacitive sensing to locate distinct droplet samples in real time. A cross-domain-optimized Butterfly-coil-input semiconductor transceiver transduces between magnetic and electrical signals to/from a sub-10 μL droplet sample for high-sensitivity μNMR screening. A temperature logger senses the ambient temperature (e.g., 0 to 40° C.) and the backend processor calibrates the working frequency for the transmitter to precisely excite the protons. In our experiments, the μNMR relaxometer quantifies avidin using biotinylated Iron NP (Φ: 30 nm, [Fe]: 0.5 mM) with a sensitivity of 0.2 μM. Auto-handling and identification of two targets (avidin and water) are demonstrated and completed within 2.2 mins. This μNMR relaxometer can achieve combinatorial chemical/biological diagnostic protocols using closed-loop electronic automation.

2. Materials and Methods 2.1 System Assembly

Figures 1A, 1B:
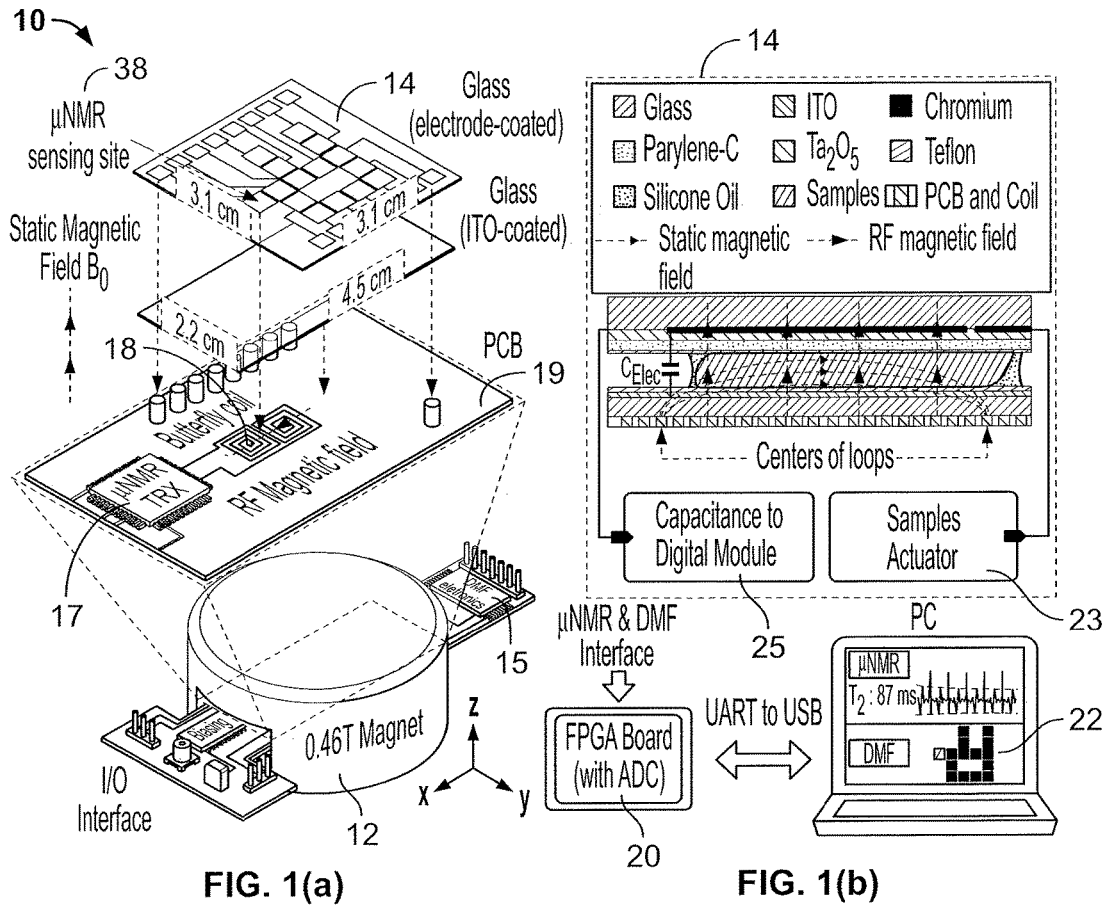
FIG. 1(a) is an illustration of a μNMR relaxometer 10 according to an embodiment of the present invention. The portable magnet 12 can greatly reduce the weight and size of the μNMR analysis, while the CMOS transceiver 17 can provide a high sensitivity, rendering it as a befitting μNMR relaxometer for POC applications. The DMF device 14 (the DMF electronics are shown by 15) is integrated with the μNMR circuitry 17 to transport the samples under analysis automatically. The Butterfly coil 18, placed directly underneath the DMF device 14, is capable of generating a magnetic field in the x direction, thus orthogonal to the static magnetic field (the z direction) and efficaciously utilizes the inner space of the magnet 12. The Butterfly coil 18 is located on the PCB 19. The μNMR circuitry is controlled by the field-programmable gate array (FPGA) board 20, which is linked with the PC 22 for display and visualization of the μNMR result and providing a graphical user interface.
FIG. 1(b) shows the brief assembly of the DMF device 14 according to an embodiment of the present invention. The droplets are squeezed inside the DMF device 14 and the Butterfly coil 18 is placed underneath the DMF device 14 for μNMR screening. The samples actuator 23 and the capacitance-to-digital module 25 form a closed-loop control to govern the location of the droplets. The step-by-step assembly as well as the operation of the μNMR relaxometer 10 is readily understood by the description and drawings provided herein including in the Electronic Supplementary Information (ESI) presented below.

An overview of the μNMR relaxometer 10 according to an embodiment of the present invention is exemplified in FIG. 1, which comprises FIGS. 1(a) and 1(b). It can be divided into two parts: a μNMR module and a DMF module. The μNMR module includes: i) a CMOS transceiver 17 to excite and receive signals from the samples; ii) a Butterfly coil 18 fabricated on the PCB 19 to transduce between magnetic and electrical signals inside the space limiting magnet 12 (e.g., volume: 28.9 cm$^3$); and iii) peripheral voltage and current regulators to power up and bias the CMOS transceiver 17. Further discussion and detail is provided in the Electronic Supplementary Information (ESI) section presented below.

The DMF module is comprised of: i) a DMF device 14 in which samples are placed and transported; ii) a samples actuator 23 that controls the pulse applied on each electrode; and iii) a capacitance-to-digital module 25 that scans the real-time capacitance of each electrode and reports the vacant sites.

Figures 2A, 2B, 2C:
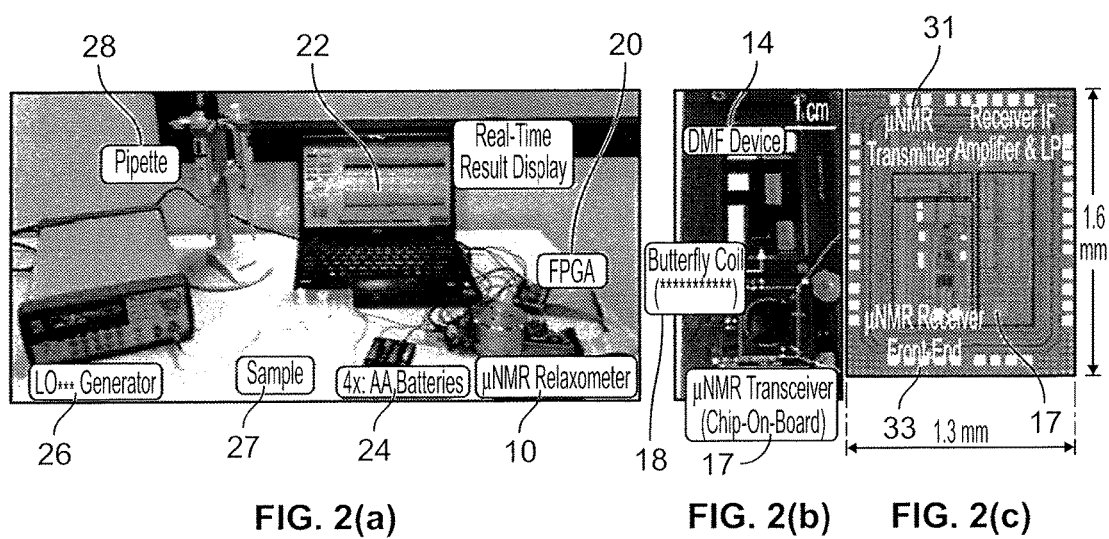
FIG. 2(a) shows the entire setup of the μNMR relaxometer 10 and peripheral devices according to an example embodiment of the invention including the FPGA 20 to control the device level hardware, the PC 22 for real-time results display and setting up of the experimental parameters (e.g., pulse width, number of echoes, echoes spacing, etc.), batteries 24 for powering up the μNMR relaxometer 10, and a signal generator 26 to provide an $LO_{ref}$ signal for the relaxometer 10. The samples 27 are placed inside the DMF device 14 using for example the pipette 28 before the experiments.
FIG. 2(b) shows the assembly of the CMOS μNMR transceiver 17, the DMF device 14, and the Butterfly coil 18 according to an example embodiment of the present invention. The DMF device 14 is placed atop the Butterfly coil 18, which is connected to the μNMR transceiver 17 to excite the samples inside the DMF device 14 and sense the resultant RF signal.
FIG. 2(c) is a photo of the CMOS transceiver die. The overall size of the die is 1.6×1.3 $mm^2$ in this example embodiment.

An experimental setup is depicted in FIG. 2(a). The system operation is centralized in the personal computer (PC) 22, including setup of μNMR parameters, display of μNMR results, and droplet routing and positioning. The PC 22 is linked with a Field Programmable Gate Array (FPGA) board 20 to control the device-level hardware using the universal asynchronous receiver/transmitter (UART). The key functional blocks and their intercommunication are detailed in the ESI section below.

2.2 μNMR Principle

The principle of NMR and μNMR is to observe the resonant behaviour of the non-zero spin nuclei (i.e., $^1H$, $^{13}C$, $^{17}O$ and $^{31}P$, etc.) with radio-frequency (RF) exciting signals acting on them in the presence of an orthogonal static magnetic field $\overline{B_0}$. With $\overline{B_0}$ acting on the non-zero spin nuclei, they magnetize in the direction of $\overline{B_0}$ and stay in equilibrium. If an excitation RF signal with frequency equal to the Larmor frequency of the nuclei applies on the nuclei orthogonally, the nuclei start to precess around $\overline{B_0}$ as a process to exchange resonant energy between RF magnetic fields and nuclear spins, and hence the net magnetization will deviate from $\overline{B_0}$ with tip angle θ. The nuclei will not precess if the excitation signal falls outside of this Larmor frequency, which can be derived as:

$$f_L = \gamma * B_0 \qquad (1)$$

with the gyromagnetic ratio of the nuclei γ. After a certain period the magnetization vector is tipped away from $\overline{B_0}$ with θ=90° and the excitation signal will be turned off. The nuclei will still oscillate at $f_L$ and decay exponentially at $T_2$ which is influenced by the environment sensed from the nuclei. This parameter can reveal the physical properties of the samples.

2.3 DMF Device and Electronic

The DMF device 14 shown in the inset of FIG. 1 comprises two parallel glass plates fit into (in this example embodiment) the 32-mm inner width of the magnet 12. The top plate (thickness: 1.5 mm) is coated with 15 Chromium electrodes (each 3.5×3.5 mm$^2$) first for droplet control, followed by multi-layer dielectric materials to enhance the EWOD force thus reducing the threshold driving voltage.[21] The ITO (Indium Tin Oxide) coated glasses were purchased from HuaNan Tehnology Ltd. (China) to serve as bottom plate of DMF device. The specified sheet resistance of the ITO is 100 Ω/sq. It serves as the ground and has a thickness of 0.5 mm, 3× thinner than the top plate rendering it suitable for μNMR screening underneath. The final coating for both plates is a hydrophobic Teflon® layer for smooth droplet actuation. Details about the fabrication procedure of the DMF device 14 can be found in ESI. The volume of liquid under testing per electrode (without mixing) is 8 μL unless specified. The DMF device 14 and its assembly are depicted in FIG. 2(*b*). (It is of course to be understood that the various dimensions and specifications given in the example embodiments presented in this disclosure are by way of illustration and example only, and that the present invention is not necessarily limited by the specific specifications given.)

Figure 18:
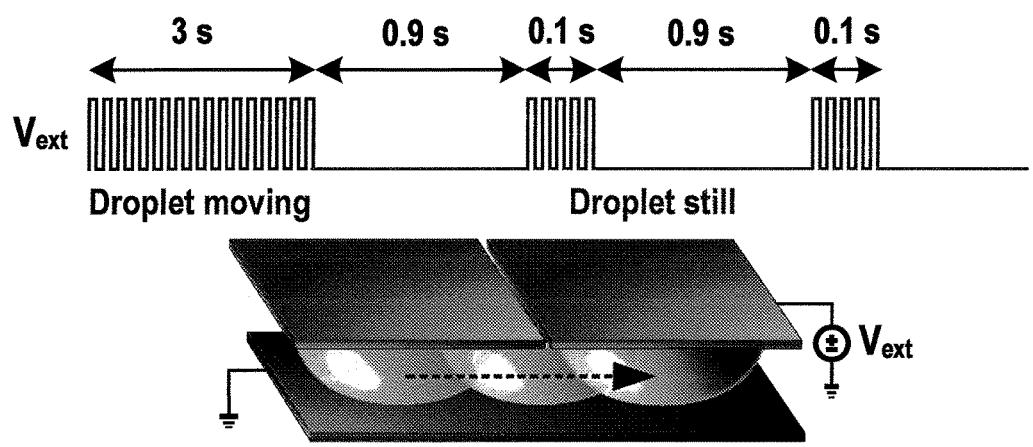
FIG. 18 shows a visualized waveform applied on an electrode before and after the droplet arrives at the electrode according to an example embodiment.

The electrodes are actuated in this embodiment by a 40-$V_{pp}$ square wave with frequency of 1 kHz. The on (off) duty cycle is 10% (90%) to strap the droplets, while reducing the RMS-voltage stress on the electrode to minimize the risk of dielectric breakdown (see FIG. 18 referred to in the ESI section below). This driving signal on the NMR sensing site is switched off during NMR experimentation to prevent interference on the sensitive NMR receiver. To further enhance the portability of the system, an electronic boost converter is used to generate the square wave so as to circumvent the use of an extra high voltage supply. The position of the droplet is sensed by a capacitance-to-digital module. A detailed schematic of the DMF electronic in this example embodiment is included in the ESI section below.

2.4 Portable Permanent Magnet

According to this example embodiment a portable magnet PM-1055 from Metrolab Technology SA (Switzerland) is adopted in this system with a nominal magnetic field of 0.5 T (±0.05 T). The portable magnet 12 has an opening gap with a dimension of 32 mm×14 mm and a weight of 1.25 kg. The magnetic field at different temperatures is measured by a Tesla Meter DTM-150 with probe LPT-130 from Group3 Technology Ltd. (New Zealand) inside temperature chamber SH-261 from ESPEC North America, Inc. (Hudsonville, Mich.).

2.5 Samples

De-ionized water was tested firstly to show the functionality of the μNMR relaxometer 10. Silicone oils (polydimethylsiloxanes) of 1 cSt viscosity from Clearco Products Co., Inc. (Bensalem, Pa.) were used as filler medium to smoothen the droplet movement due to their low surface tension, and prevent sample evaporation. Copper (II) sulfate solutions were prepared from $CuSO_4.5H_2O$ purchased from Aladdin® (Industry, Calif.). Avidin powder was purchased from Sigma-Aldrich Co. (St. Louis, Mo.) and biotinylated magnetic NP (Φ: 30 nm) were purchased from Nanocs Inc. (New York, N.Y.). The concentration of biotinylated magnetic NP throughout the experiment is 0.5 mM.

2.6 μNMR CMOS Transceiver

The μNMR transceiver 17 in this example embodiment was designed in a 0.18-μm CMOS process by EDA tool Vituoso Platform from Cadence Design Systems, Inc. (San Jose, Calif.) and fabricated by GlobalFoundries Inc. (Santa Clara, Calif.) with one polysilicon layer and six metal layers. The photo of the die is shown in FIG. 2(*c*). The transmitter 31 is equipped with a state control and pulse sequence synthesizer 35, and a power amplifier to generate the Carr-Purcell-Meiboom-Gill (CPMG) pulse sequences and excite the samples via the Butterfly coil 18. For the receiver 33, it is headed by a multi-stage low-noise amplifier 60 to boost the gain and enhance the signal-to-noise ratio (SNR) of the experiments, followed by a pair of quadrature mixers 62 downconverting the RF signal to intermediate frequency (IF) for filtering. A dynamic-bandwidth lowpass filter 64 was designed to rapidly recover from the dead time and manage the uncertain IF. The filter 64 is a $6^{th}$-order Butterworth using the source-follower-based topology. The overall receiver 33 has a simulated input-referred noise of 0.92 nV/√Hz. The die is bonded on the PCB 19 by chip-on-board technology with encapsulated sealing to reduce the lead inductance.

The CMOS transceiver 17 is powered up, e.g., by batteries or another suitable power supply and regulated with a 1.8-V low-dropout regulator. The Butterfly coil 18, which transduces between magnetic field and voltage signals, can effectively utilize the inner space of the magnet 12 by generating a surface-parallel RF-magnetic field orthogonal to the static magnetic field. The Butterfly coil 18 was fabricated on the PCB 19 with a conductor width of 0.15 mm and spacing of 0.15 mm. The coil's parameter and geometry optimization were studied in finite element analysis simulator COMSOL Multiphysics® (Burlington, Mass.) and this is detailed in the ESI section below. The signal generator 43 (33250A from Agilent Technologies, Santa Clara, Calif.) served as a voltage-controlled oscillator, providing an $LO_{ref}$ signal for the μNMR relaxometer 10, which can be replaced by, e.g., an on-chip phase-locked loop or other suitable circuit if desired. The temperature sensor MAX6612 from Maxim Integrated (San Jose, Calif.) is utilized to sense the ambient temperature. A detailed design and schematic according to an example embodiment as well as the measurement result of the CMOS transceiver 17 and the peripheral electronics are discussed in the ESI section below.

2.7 μNMR Experimental Parameters

The π/2 pulse widths for the Butterfly coil 18 was found to be 150 μs. A CPMG pulse sequence was used to excite the protons and refocus the dephasing magnetization attributed to the inhomogeneous magnetic field. Relaxometry is chosen for this system as it poses a flexible requirement on the magnet 12, hence the volume and weight of the magnet 12 can be reduced compared to its spectroscopy counterpart, rendering it favourable to POC diagnosis. Spacing between the echoes were set to 4 ms for all cases. The samples were halted for 6 s upon arrival on the μNMR sensing site for the stabilization of the hydrogen nuclei. The experiments were repeated 8 times to enhance the SNR and the time interval between the successive experiments was set at 6 s.

2.8 μNMR Signal Post-Processing

The μNMR results were recorded and digitized by an Analog-to-Digital Converter ADC128S022 from Texas Instruments Inc. (Dallas, Tex.) with 12-bit resolution. Thereafter the raw data were sent to the PC 22 and the I/Q channel data were demodulated with a Hilbert transformer to reject the image noise. The spin-spin relaxation time was derived by a nonlinear regression model. The $T_2$ spectrum of the samples was obtained by performing inverse Laplace transform on the echoes amplitude in MATLAB from MathWorks, Inc. (Natick, Mass.).

3. Results 3.1 Temperature-Tracking $LO_{ref}$ Generation

The Neodymium magnet is sensitive to temperature (stated −1200 ppm/K). Thus, albeit in room temperature, the Larmor frequency of proton shifts ~25.5 kHz per 1° C. variation. Confounded by the narrow bandwidth of the excitation signal (18.8 kHz for 300 μs refocusing pulses) attributed to the low voltage CMOS transceiver 17, this frequency shift may cause the μNMR relaxometer to malfunction, and calibration of the local oscillator ($LO_{ref}$)

frequency is hence necessitated. To achieve this, a temperature-tracking $LO_{ref}$ generator 26 was developed.

Figure 3:
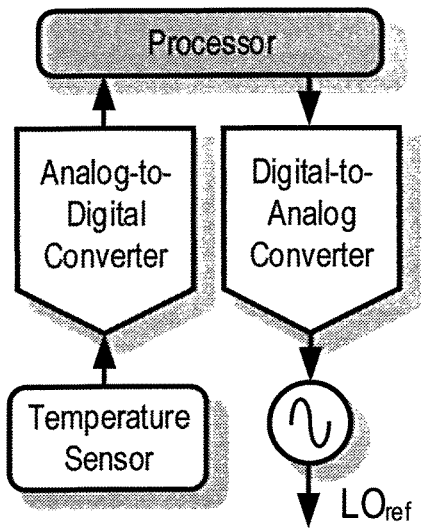
FIG. 3(a) shows the schematics of the temperature-tracking $LO_{ref}$ generator 26 according to an example embodiment. A temperature sensor 30 is used to sense the ambient temperature and the result is digitized by the analog-to-digital converter 29 and read by the processor 32. The required working frequency for the $LO_{ref}$ is then calculated by the processor 32 and the processor 32 drives the digitalto-analog converter 34, which alters the output frequency of the signal generator 43 thus befitting with the Larmor frequency of the protons.
FIG. 3(b) shows the measured result of the magnetic field of the magnet 12 and temperature sensor 30 output over temperature. Both of them show a great linearity (R2>0.999) hence the required $LO_{ref}$ frequency can be calculated from the temperature sensor output.
Figure 3:
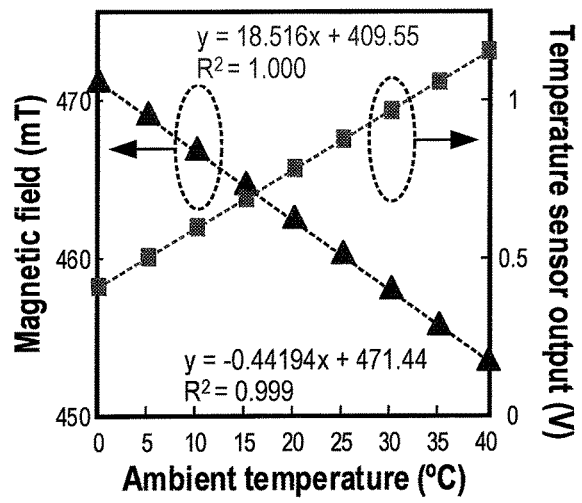

Illustrated in FIG. 3(*a*), a temperature sensor 30 detects the ambient temperature, and the processor 32 (a portable computer or PC here, but any suitable processor will do) reads the corresponding digitized value and calculates the corresponding temperature. Consequently, the processor 32 can calibrate the required working frequency for the $LO_{ref}$ and drive the digital-to-analog converter (DAC) 34 with a proper code. The output of the DAC 34 is fed into the signal generator 43 and the frequency of the $LO_{ref}$ is altered by the output of the DAC 34, thus matching the Larmor frequency of the proton, which is shown in eqn. (1) linearly proportional to the magnetic field, with the excitation frequency.

FIG. 3(*b*) depicts the magnetic field and temperature sensor 30 output versus temperature. Both of them show a linear relationship with the temperature and thus the Larmor frequency can be calibrated from the temperature. This feature enables the system to work in an environment with ambient temperature ranges from approximately 0 to 40° C., while raising the robustness of the μNMR relaxometer 10.

3.2 Operation of Water Droplet

Figures 4A, 4B, 4C:
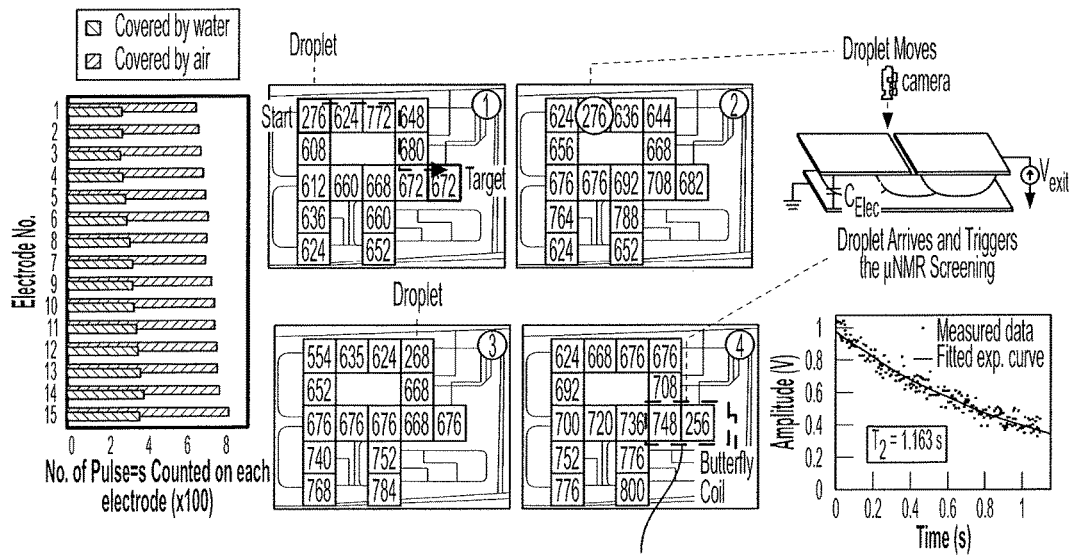
FIG. 4(a) shows the pulses counted on the electrodes covered by air and water, respectively. As the permittivity of water is substantially larger than air (80:1), the capacitance of the electrode covered by water has a higher capacitance, causing lower pulses counted and thus the system can detect if the electrode is vacant.
FIG. 4(b) show photos taken outside the magnet 12, which demonstrate the movement of the droplets. The real-time pulses counted on the electrodes are marked respectively. The droplet is initially placed on an arbitrary electrode (e.g., the upper left in the photo) and the system detects the location of the droplet by comparing the pulse counted on the electrodes. After the droplet is located, it is guided to the μNMR sensing site 38 progressively (from 1 to 4).
FIG. 4(c) shows that once the droplet arrives at the μNMR sensing site, the μNMR experiment or screening will be triggered and the echoes amplitude of the samples will be collected (e.g., 256 echoes). The visualized operation of the μNMR relaxometer 10 can be displayed.

FIG. 4(*a*) shows the pulses counted on the electrodes covered by air and water, respectively. As the permittivity of water is substantially larger than air (80:1), the capacitance of the electrode covered by water has a higher capacitance, causing lower pulses counted and thus the system can detect if the electrode is vacant.

A de-ionized water sample was experimented with to demonstrate the functionality of the μNMR relaxometer 10. The droplet was placed on an arbitrary electrode and the DMF device 14 can auto-locate the droplet by scanning and comparing the pulses counted in each electrode. With a droplet sandwiched between the electrode and the ITO, the capacitance of the corresponding electrode rises as the permittivity of water is 80× of air. As shown in FIG. 4(*a*), the average pulse counted on the occupied and vacant electrodes were 277.5 and 757.7, respectively. This 2.73× difference suffices to identify whether the electrodes are occupied by the droplets. This sensing module is critical in this two dimensional DMF device as the relaxometer 10 entails handling of multiple droplets. As well, with this sensing module adopted, the system is under a close-loop control to attain an efficient droplets management scheme. The operation of the droplets including the trigger of the NMR experiment, stabilization of the hydrogen nuclei before the NMR experiment, and anti-merging droplets paths can be manipulated and optimized by the software within the shortest time to boost the efficiency and throughput of the system.

After identification of the droplet location, the program starts to transport the droplet to the μNMR sensing site 38. FIG. 4(*b*) show photos taken outside the magnet 12, which demonstrate the movement of the droplets. The real-time pulses counted on the electrodes are marked respectively. The droplet is initially placed on an arbitrary electrode (e.g., the upper left in the photo) and the system detects the location of the droplet by comparing the pulse counted on the electrodes. After the droplet is located, it is guided to the μNMR sensing site 38 progressively (from 1 to 4). FIG. 4(*c*) shows that once the droplet arrives at the μNMR sensing site, the μNMR experiment or screening will be triggered and the echoes amplitude of the samples will be collected (e.g., 256 echoes). The visualized operation of the μNMR relaxometer 10 can be displayed.

Thus, as can be seen from the example shown in FIG. 4, the droplets are guided to the destination gradually with their positions tracked in real-time to ensure successful movement. To visualize these movements, the entire journey was recorded outside the magnet as shown in FIG. 4(*b*). The droplets are transported with a velocity of 1.17 mm/s (i.e., 3 s per electrode). Snapshots of a droplet moving between neighbouring electrodes are shown in FIG. 20, explained further in the ESI section below. Upon the droplet arrival, the μNMR experiment or screening is triggered after 6 s and the $T_2$ of the sample is derived as depicted in FIG. 4(*c*) by applying the CPMG pulse sequence on the droplet. The CPMG pulse sequence can recover the hastened damping NMR signal attributed to the field inhomogeneity of the magnet by refocusing the dephasing spins across the droplet.

Figure 5A:
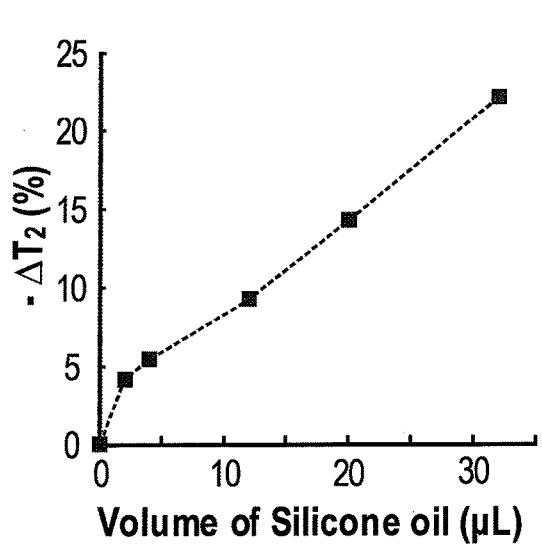
FIG. 5(a) is a graph illustrating the interference of silicone oil on $T_2$ of deionized water. As the amount of silicone oil surrounding the droplets increases, the $T_2$ deviates from its original value (without silicone oil).
Figure 5B:
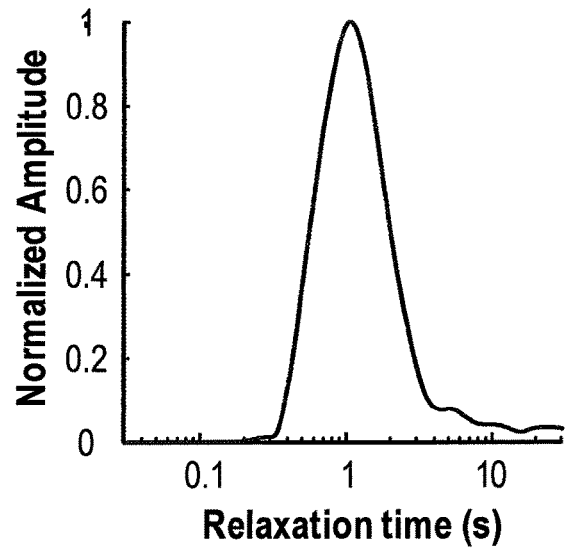
FIG. 5(b) is a graph illustrating the $T_2$ spectrum of the samples enclosed with 1.6 μL of Silicone oil, showing a singular exponential decay for the samples.

Silicone oil is commonly utilized in DMF to smoothen the droplet operation. Yet it contains hydrogen atoms (formula: $[—Si(CH_3)_2O—]n$) that will affect the μNMR result. To evaluate the interference from the silicone oil, the $T_2$ variation of the samples (i.e., water) with different volume of silicone oil is showed in FIG. 5(*a*). With increasing amount of silicone oil, the $T_2$ of the sample deviates from its original value. A volume of 1.6 μL of silicone oil shell (<0.1 mm) was chosen to surround the samples for minimum interference to the μNMR result ($\Delta T_2$<5%), while preserving its function in smoothening the droplet motion. The $T_2$ spectrum of the resulting samples and oil formation is plotted in FIG. 5(*b*), showing the desired single decaying exponential pattern.

3.3 Chemical/Biological Samples Quantification

Figure 6A:
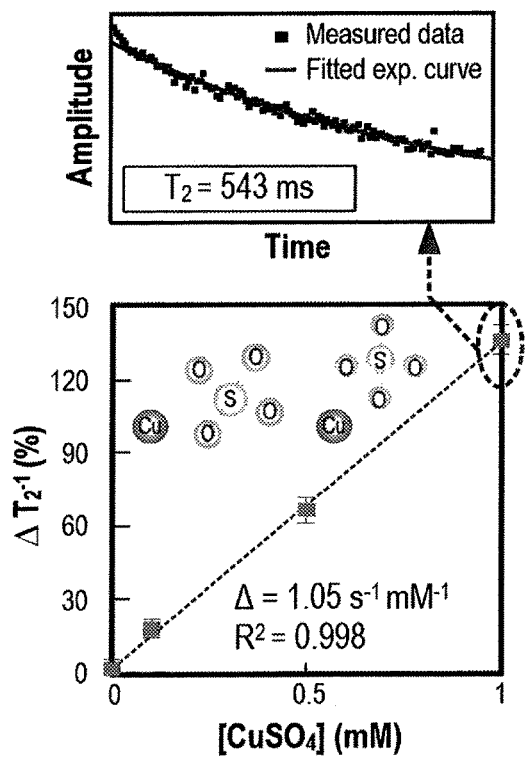
FIG. 6(a) is a graph illustrating the correlation of $\Delta T_2^{-1}$ (reference to 0 mM of $CuSO_4$) to concentration of $CuSO_4$, which shows a linear dependency. The paramagnetic $CuSO_4$ ions perturb the local field and thus shorten the $T_2$ of the protons. The echoes amplitude for the case of $CuSO_4$ with 1 mM concentration is plotted above. 128 echoes are collected for each single experiment.
Figure 6B:
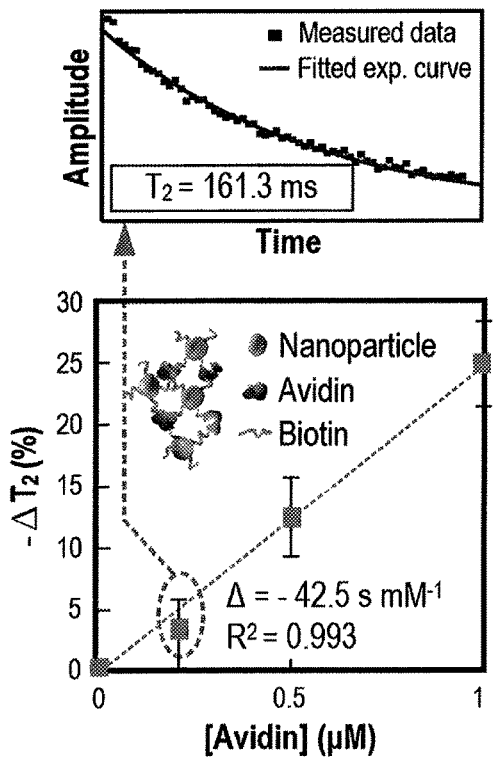
FIG. 6(b) is a graph illustrating the correlation of $\Delta T_2$ (reference to 0 μM of avidin) to the concentration of avidin, which shows a linear dependency. Avidin bonds with biotin which is attached on the Iron NP and forms NP microclusters and thus shortens the $T_2$ of the samples. The echoes amplitude for the case of avidin with 0.2 μM concentration is plotted above. 64 echoes are collected for each single experiment.

The capability of quantifying chemical and biological targets of the μNMR relaxometer was studied. Paramagnetic $CuSO_4$ ions have a high magnetic susceptibility of 1330× $10^{-6}$ $cm^3$ $mol^{-1}$. It will perturb the local field of the surrounding protons and shorten the $T_2$, and thus it is used as the test agent in the first experiment. As shown in FIG. 6(*a*), the μNMR relaxometer can detect the $CuSO_4$ concentration with $T_2^{-1}$ increases linearly.

The second experiment demonstrates the capability of the system to pinpoint specific biological targets with a pre-designed probe-decorated NP. Iron NP with biotin labeling are used as probe to quantify avidin in the samples. The biotinylated magnetic NP bond with avidin to yield NP micro-clusters, which shorten the $T_2$ of the proton attributed to super-paramagnetism of Iron NP. FIG. 6(*b*) depicts the experimental result, which shows that the $T_2$ value decreases proportionally to the concentration of avidin with an achieved sensitivity of 0.2 μM. These experiments evince that the μNMR relaxometer is capable of handling and quantifying chemical and biological targets.

3.4 Multi-Step Multi-Sample Droplet Operation

One unique feature of the μNMR relaxometer of the present invention is the capability to handle distinct samples and perform μNMR experiments on them sequentially. This is attributed to the expanded two-dimensional electrodes beneficial from the compact CMOS transceiver 17. The feature is demonstrated by placing two stationary targets and two identical probe-decorated NP droplets inside the DMF device 14 at the same time. Since the relaxometer 10 in this embodiment has to handle multiple samples, it is crucial to distinguish the droplets and project individual paths for them without the risk of fortuitous mixing. As the location of the droplets can be tracked by the capacitance-to-digital module, their individual paths can be procured at the software level.

As shown in FIG. 7(*a*), the $1^{st}$ probe-decorated NP droplet (7.5 μL) is guided to a stationary target 40 (2.5 μL) for mixing, then to the μNMR sensing site 38 to extract the $T_2$. Concurrently, the $2^{nd}$ probe-decorated NP droplet is guided to another target 42 for mixing. The 1st mixture is led away from the µNMR sensing site 38 after finishing the diagnosis (here, in 48 s), allowing the 2nd mixture to come in. The assays are completed after the 2nd mixture finished µNMR screening and the raw data is processed in the PC 22 for concentration quantification ($T_2$ of water sample: 256 ms; avidin: 211 ms). Two or more probes and targets pairs can be placed inside the DMF device 14 for enhancing the throughput of the relaxometer 10, depending on the geometry of the DMF electrodes.

The timing diagram of the µNMR relaxometer operation in this example is shown in FIG. 7(b). With the droplet movement controlled by the program automatically and their positions tracked in real-time, optimization of the route and timing management can be done at the software level. The fastest protocol can be found and applied to the DMF device 14. This 2.2-min experiment validates the entire system as being capable to transport, mix and analyze multiple distinct samples in real-time, while reducing the labor work (error) and the risks of defilement.

Another experiment reveals the capability of the relaxometer to handle the sample prior/after the NMR sensing. A droplet which acts as a probe (water) is placed on an arbitrary position inside the DMF device 14 together with two targets 50, 50 (2 nanomole of $CuSO_4$ individually), as shown in FIG. 8(a). Firstly the probe 52 is guided to the sensing site 38 for recording the original $T_2$. Afterwards the droplet 52 is guided to another electrode and mixed with the 1st target 50. The $T_2$ of the resultant mixture is then recorded for concentration identification. Subsequently the droplet 52 is moved to another electrode and is mixed with the 2nd target 50 and the $T_2$ of the mixture is analyzed again at the sensing site 38. Illustrated in FIG. 8(b), this experiment successfully pinpoints the amount of analytes existing in multiple targets in a multi-step fashion, benefiting from the droplet management capability and the expanded DMF electrode array, for the relaxometer 10 of the present invention.

4. Discussion

Figure 9:
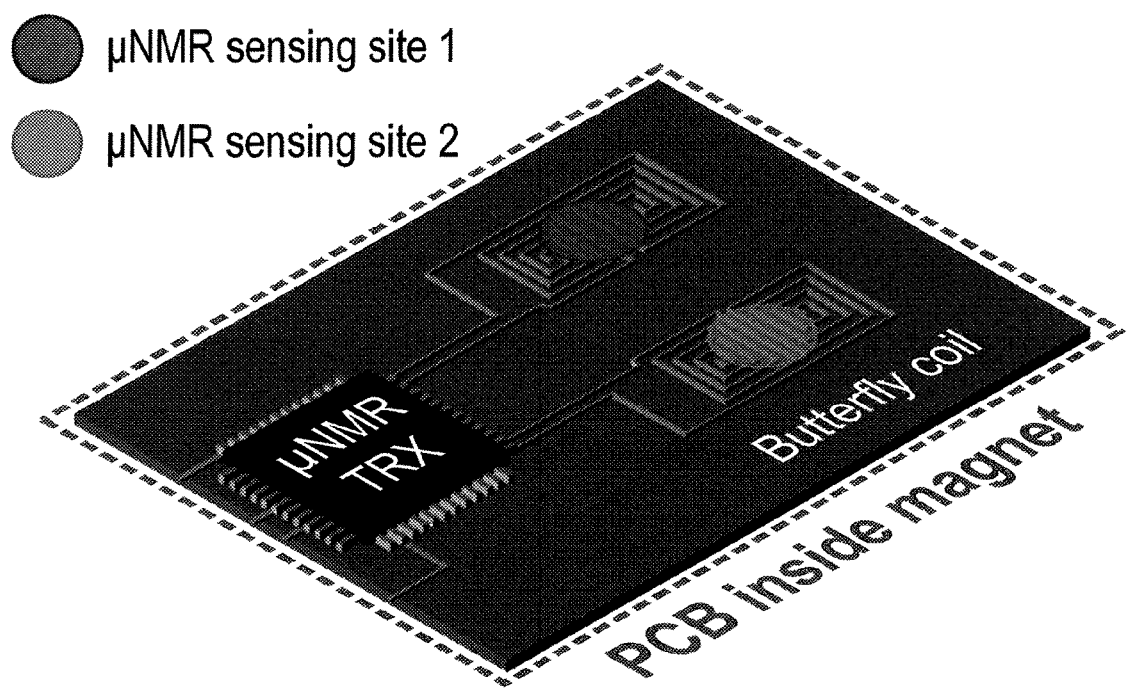
FIG. 9 is an illustration of the multi-butterfly-coil μNMR relaxometer according to an example embodiment of the invention. By integrating multiple receivers inside the CMOS transceiver together with multiple butterfly coils 54, 56, the throughput of the assay can be further increased to befit a simultaneous multi-biomarker targeting. For simplicity the DMF device 14 is omitted in this figure.

The electronic-automated µNMR relaxometer of the present invention surpasses existent µNMR systems as it can simultaneously quantify multi-biomarkers in a single experimental setup by manipulating the samples utilizing the DMF device 14 as demonstrated in the experiments. In addition to the time-multiplexing assay, the throughput can be elevated by adopting multiple butterfly coil 18 inside the magnet 12. As depicted in FIG. 9, a transceiver built with multiple receivers can be used to receive and process the signals from multiple butterfly coils 54, 56 for higher throughput and space utilization.

Additionally, attributed to the non-invasive and contactless properties of µNMR, this µNMR relaxometer 10 integrated with a DMF device 14 can be extended by introducing other DMF-compatible protocols to further enhance the applicability of the system. Exemplification includes cell isolation, cell culturing, DNA amplification, and electroimmunoassay inside the DMF device 14. These protocols can be utilized with extant NMR analytic techniques to culminate in a unified and integrate solution for lab-on-a-chip assay. In addition, a thermal heater can also be integrated inside the DMF device 14 to alter the temperature of the droplets, which opens up the capability of temperature related NMR assays on biological samples. Furthermore, multimodal analysis in which different aspects of the sensing technique such as optical sensing or impedance sensing combined with the µNMR system can be implemented inside the DMF device 14 to provide complementary analytes information.

5. Conclusions

The present invention in one embodiment discloses a portable µNMR relaxometer capable of handling multi-step multi-sample protocols, which is demonstrated for the first time. It is equipped with a semiconductor transceiver to reduce the overall dimensions of the module while improving the sensitivity. The transceiver's input network is a PCB-fabricated Butterfly coil to better utilize the inner space of the handheld or portable magnet. Inside the magnet, the electronic-automated DMF device with closed-loop capacitive feedback manages multiple droplet samples in real-time and can be reconfigured by software. A number of experiments validate the µNMR relaxometer as being competent to achieve real-time quantification of chemical/biological analyte in, e.g., sub-10-µL samples and capable of manipulating multiple samples automatically and performing multi-step experiments inside the space limiting magnet effectively. When compared to the conventional micro-channel NMR systems, this work, the present invention, offers a more flexible and electronic-automated method to handle multi-step multi-sample diagnostic protocols.

6. Electronic Supplementary Information (ESI)

The following Electronic Supplementary Information (ESI) provides further information and specifications regarding the present invention according to example embodiment(s) thereof, and includes:

6.1. Highlights of recent µNMR systems.

6.2. A design of the CMOS µNMR transceiver according to an example embodiment.

6.3. Simulation and measurement results of the CMOS transceiver.

6.4. Co-optimization of the butterfly coil and CMOS transceiver.

6.5. A digital microfluidic (DMF) module according to an example embodiment.

6.6. DMF device fabrication according to an example embodiment.

6.7. Droplet actuation.

6.8. µNMR relaxometer software and hardware interfaces.

6.1. Highlights of Recent µNMR Systems

Figure 10:
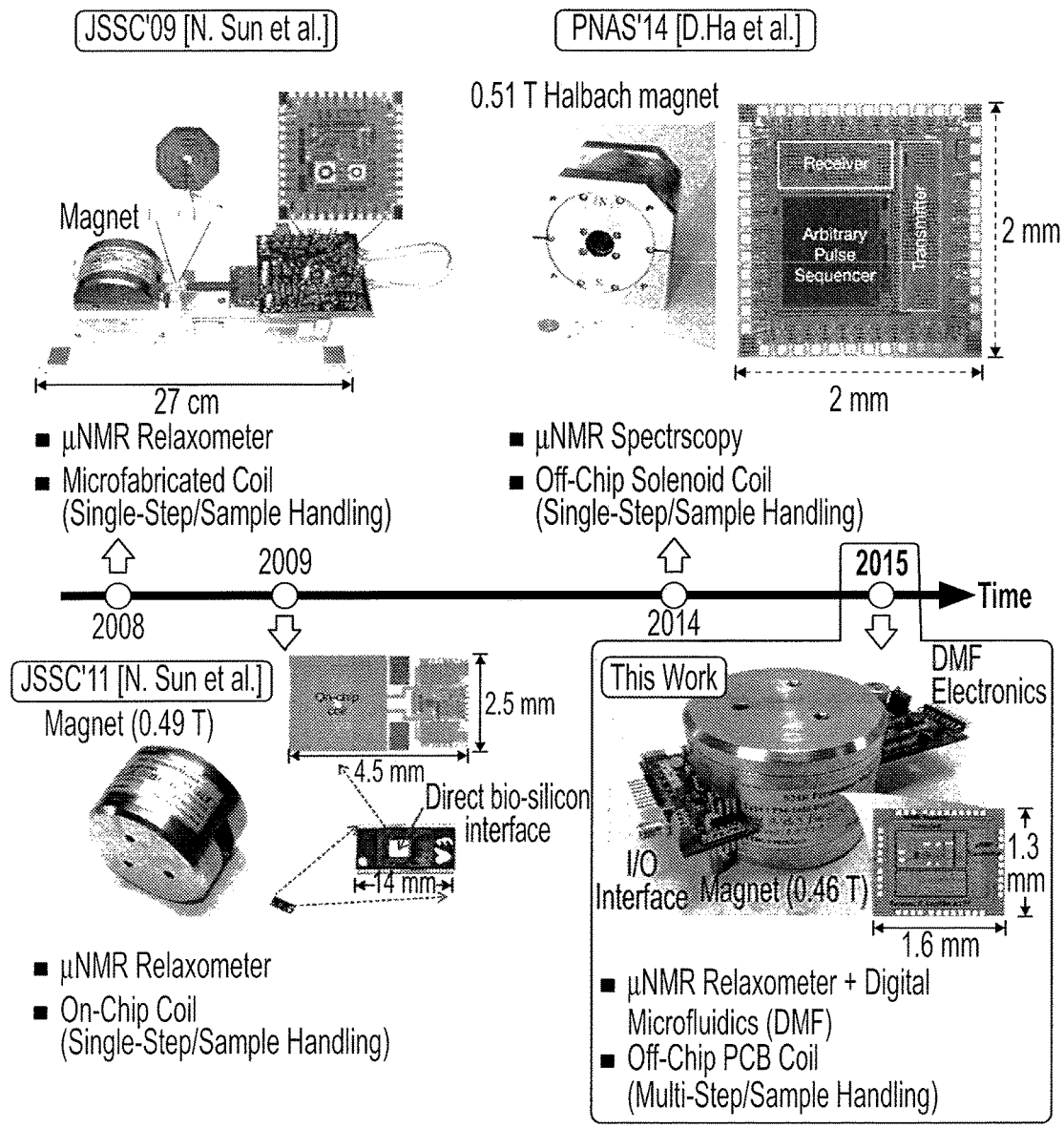
FIG. 10 shows μNMR systems developed in the last decade. The present invention according to an example embodiment (labeled "This Work" in the FIG. 10 and in Table 1) succeeds in integrating a DMF device into an μNMR relaxometer to achieve multi-step multi-sample handling inside a volume-limited portable magnet.

A brief summary of recent advancement of µNMR systems including their overall illustration together with depictions of their integrated circuits and a brief reference to the present invention ("This work") are shown in FIG. 10. The present invention succeeds in managing multiple samples under NMR assay using electronic-automated method which can decrease amount of labor work (error) and the risks of defilement. The present invention integrates the DMF device 14 into the µNMR relaxometer 10 to achieve multi-step multi-sample handling inside a volume-limited portable magnet 12.

6.2. Design of the CMOS µNMR Transceiver

The semiconductor transceiver for µNMR-signal excitation and reception in this example embodiment of the present invention was designed and fabricated in a 0.18-µm CMOS technology to optimize the overall performance and integration level. As depicted in FIG. 11, there are two parts: the transmitter 31 and the receiver 33, as detailed further below. More particularly, FIG. 11 is a schematic of the µNMR transceiver and its connection to its external parts including the Butterfly coil 18.

6.2A. Transmitter

The transmitter 31 generates a Carr-Purcell-Meiboom-Gill pulse sequence and delivers adequate signal power to the external Butterfly coil 18 to excite the nuclei of the droplet sample. An all-digital state control and pulse sequence synthesizer 35 are integrated to read the commands given from the field programmable gate array (FPGA) 20. The FPGA 20 manages the overall status of the transceiver 17, including the low-noise amplifier (LNA) stage 60, transmission switches, and low-pass filters (LPFs) 64. In addition, the synthesizer 35 will control the pulse sequence that is delivered to the power amplifier (PA) 58 with proper phase (0° or 90°), which is synthesized from the external reference signal $LO_{ref}$. The PA 58, as shown in FIG. 12(a), is realized as a differential chain of four inverter stages to optimize the output current driving to the Butterfly coil 18, while reducing the propagation delay. The size of the inverters is quadrupled sequentially to boost the output power. This class-D PA topology does not consume static current, resulting in better power efficiency. The switches controlled by the state control were inserted between the PA 58 and the Butterfly coil 18. The Butterfly coil 18 is tailored to enlarge the usability space inside the portable magnet 12.

6.2B. Receiver

The receiver 33 is to extract the weak µNMR signal induced by the Butterfly coil 18 from the protons. Outside the transceiver chip 17, a discrete capacitor $C_{ext}$ is placed in parallel with the Butterfly coil 18 for resonant pre-filtering, while offering a passive pre-gain to the signal. This is a feasible technique as the received signal is narrowband around the Larmor frequency, and thus no distortion will be added. Inside the chip 17, the receiver 33 is headed by a multi-stage LNA 60 as shown in FIG. 12(b). The LNA 60 dominates the signal-to-noise ratio of the receiver 33, as the noise contribution from the subsequent stages will be suppressed by the gain of it. The LNA 60 is optimized for low noise to avoid deteriorating the signal-to-noise ratio of the µNMR signal, whereas it should avoid immense power unsuitable for point-of-care (POC) diagnostic tools. The present invention uses a complementary common-source topology for current reuse, which provides better performances when compared with the typical common-source amplifier. The differential implementation rejects the common-mode noises picked up from the environments (i.e., electromagnetic interference and power line coupling). A common-mode feedback (CMFB) circuit 61 stabilizes the output common-mode level. Three similar LNAs (or any other suitable number) can be cascaded to amplify the signal for subsequent signal processing.

The LNA 60 is followed by two active mixers 62 for I and Q channels, as shown in FIG. 12(c), for downconverting the radio-frequency (RF) signal at 19.6 MHz to intermediate frequency (IF) signal at ~1 kHz for digitization in this example embodiment. The mixers 62 are double-balanced to reduce the noise figure (double sideband) and feedthrough from the local oscillator (LO) to the IF. The 4-phase LO is provided by the pulse sequence synthesizer 35. The mixers 62 are constructed in this embodiment by PMOS transistors to reduce the flicker noise and substrate coupling from/to another part of the chip 17.

The downconverted µNMR signal will be further processed by the LPFs 64, which suppress the out-of-band noise and unwanted high-frequency products generated by the hard-switched mixing process. The LPFs 64 are implemented as a $6^{th}$-order Butterworth using the source-follower-based topology, visualized in FIG. 12(d). Such topology features a transistorized positive-feedback technique to build a complex pole in a single branch, reducing the circuit complexity and unwanted parasitic poles. Assuming $M_1$ and $M_3$ have a transconductance $g_{m1}$, and $M_2$ and $M_4$ have a transconductance $g_{m2}$, the transfer function and corresponding cut-off frequency of each Biquad are given by:

$$H(s) = \frac{1}{s^2 \frac{C_1 C_2}{g_{m1} g_{m2}} + s \frac{C_2 g_{m1} - C_2 g_{m2} + C_1 g_{m2}}{g_{m1} g_{m2}} + 1} \quad \text{(S1)}$$

$$\omega_0 = 2\pi f_0 = \sqrt{\frac{g_{m1} g_{m2}}{C_1 C_2}} \quad \text{(S2)}$$

As $g_m$ of the transistor is proportional to the square root of its bias current, the cutoff frequency can be adjusted by controlling the bias current. This aim avoids the use of large resistors or capacitors which are costly in integrated circuits. In addition, unlike the fixed-resistor-capacitor LPFs, the bandwidth of this kind of LPF is tunable by altering the bias current of the transistors, being more area-efficient for bandwidth control. Two PMOS-type Biquad and one NMOS-type Biquad are cascaded to construct the $6^{th}$-order Butterworth response, while matching their input and output common-mode levels.

The selected LPF's bandwidth is critical to the quality of the final received µNMR signal. Excess bandwidth will raise the out-of-band noise, but inadequate bandwidth will distort the signal, thus penalizing the accuracy of the result. The excitation pulses will affect the output DC level, and thus it will affect also the DC level of the following echo signals and distort the result.

Figure 13:
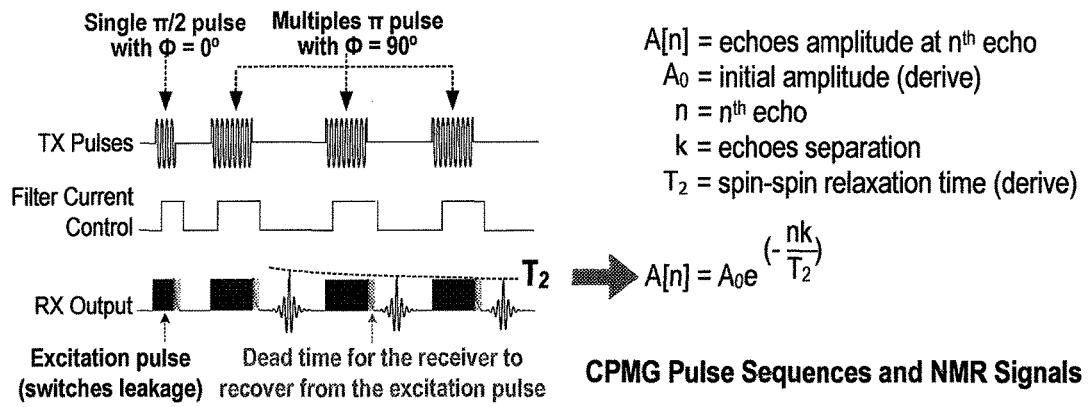
FIG. 13 is a timing diagram of the CPMG pulse sequences and the receiver output response showing the dead time of the receiver caused by the excitation pulses. Echoes amplitude of the NMR signals is also shown in the figure.
Figure 14:
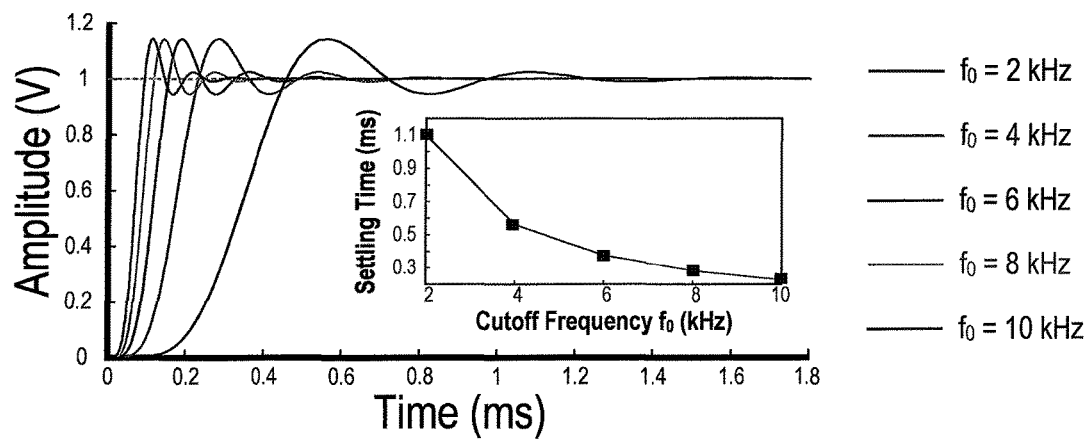
FIG. 14 is a graph showing the step response of the 6th-order Butterworth LPF according to an example embodiment for the LPF 64 with different cut-off frequencies $f_0$. The inset shows the corresponding settling times.

FIG. 13 is a timing diagram of the CPMG pulse sequences and the receiver output response showing the dead time of the receiver 33 caused by the excitation pulses. Echoes amplitude of the NMR signals is also shown in the figure. More specifically, as shown in FIG. 13, even there are isolation switches to prevent the excitation pulses from saturating the receiver, there are still leaking pulses that may appear at the output due to non-ideal switches, causing a dead time for the receiver. Yet, with a small bias current, the duration of recovery from the dead time caused by the excitation pulse will be longer. Simulated in MATLAB, the step responses of an ideal $6^{th}$-order Butterworth LPF with a bandwidth from 2 to 10 kHz are shown in FIG. 14, where the inset shows the settling time of the LPF 64 at different cutoff frequencies. The settling time is inversely proportional to the cutoff frequency, posing a tight trade-off between the receiver's noise and settling time if the bandwidth is fixed. Herein the present invention discloses a dynamic-bandwidth LPF topology to break such a trade-off. As shown in FIG. 13, the bandwidth of the LPF 64 is expanded during the excitation mode to swiftly recover from the excitation pulse, while its bandwidth is shrunk in the stable receiving mode to reduce the out-of-band noise.

Subsequent to the LPFs, voltage buffers implemented as a simple source-degenerative common-source amplifier with a gain of 2 V/V are adopted to drive the off-chip analog-to-digital converters, which are enclosed within the FPGA board 20 for digitization.

6.3. Simulation and Measurement Results of the CMOS Transceiver

The CMOS transceiver 17 of this example embodiment is power-up via low-dropout regulators ADP323 from Analog Devices Inc. (Norwood, Mass.) and current regulators LM334 from Texas Instruments Inc. (Dallas, Tex.). Measurement results show the transmitter 31 draws 19.6 mW power in transmitting mode, whereas the PA 58 dominates the power consumption (>99%). The PA 58 has a high power efficiency of 28% and provides an effective RF field of 5.7 Gauss on the samples.

The receiver 33 has a simulated gain of 87.6 dB at 20 MHz with an input-referred noise of 0.92 nV/√Hz for each channel. The measured power consumption of the receiver 33 is 26.6 mW, with the forefront LNA consumes prodigious power (18.0 mW), as a large bias current is entailed to suppress the noise.

Figure 15:
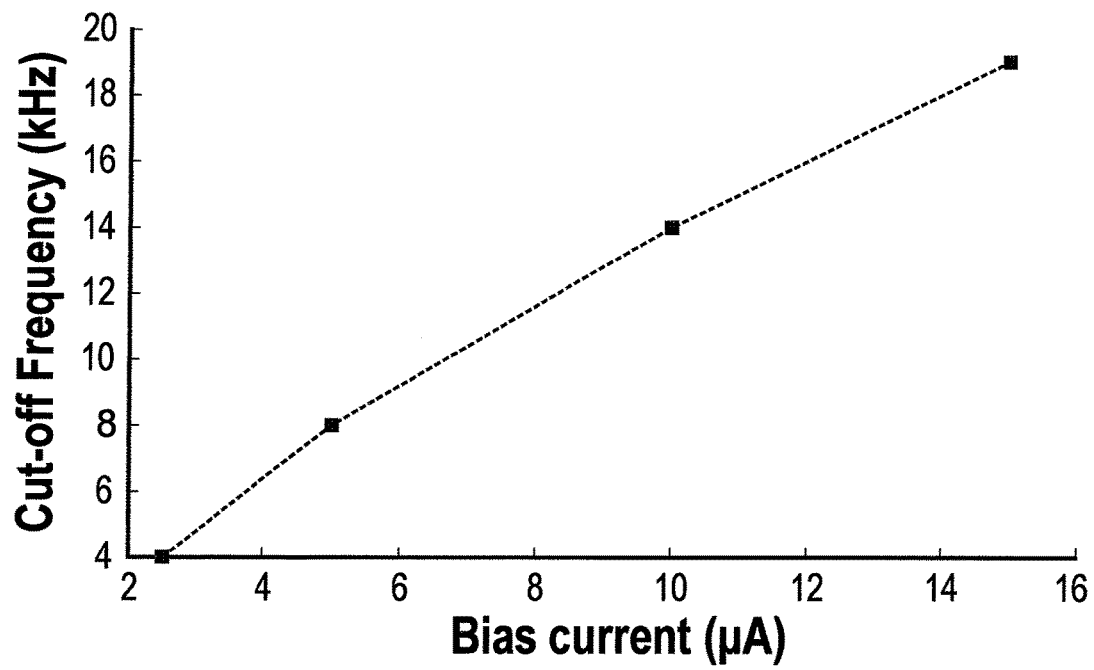
FIG. 15 is a graph showing the relationship between the cut-off frequency of the LPF 64 and its bias current in this example.

FIG. 15 shows the relationship between the LPF's cut-off frequency and its bias current; that is, this figure shows the bandwidth of the LPF versus the bias current as measured. With a large bias current, the $g_m$ of the transistors will be raised up, causing the cut-off frequency of the LPF 64 to be increased as predicted in Eqn. (S2). Thus, the dynamic-bandwidth tuning can be achieved by altering the bias current of the LPFs during the excitation and receiving modes. This method can preserve a low out-of-band noise while shortening the effect of the switch leakages during the excitation mode.

6.4. Co-Optimization of the Butterfly Coil and CMOS Transceiver

Figure 16A:
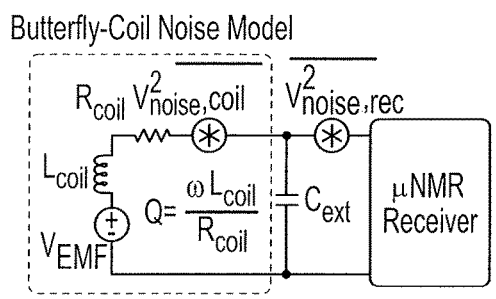
FIG. 16(a) shows a noise equivalent circuit of the receiver 33 front-end with the Butterfly coil 18 according to an example embodiment of the present invention.

The geometry (i.e., number of turns) for the Butterfly coil 18 is closely related to the SNR of the µNMR receiver. The induced voltage $V_{EMF}$ of the coil can be expressed as:

$$V_{EMF} = -\int \left(\frac{\partial}{\partial t}\right)(B_1 M_0) dV_s \tag{S3}$$

with the nuclear magnetization $M_0$, the RF magnetic field produced by the unit current passing through the Butterfly coil $B_1$ and the volume of the droplet $V_S$. The $V_{EMF}$ of the different Butterfly coils thus can be compared by averaging $B_1$ acting on the droplets provided that the magnetization of the nuclei and the volume and shape of the droplet are the same for both cases. Consequently, the thermal noise for the conductor of the Butterfly coil can be expressed by the Nyquist formula:

$$\overline{V^2_{noise,coil}} = 4k_g T_{coil} R_{coil} \tag{S4}$$

with the Boltzmann's constant $k_B$, the resistance of the Butterfly coil path $R_{coil}$ and absolute temperature of the conductor $T_{coil}$. Both the induced voltage and the thermal noise are amplified with a passive gain $\sqrt{Q^2+1}$ offered by the LC-tank where Q is the quality factor of the Butterfly coil. Depicted in FIG. 16(a), the SNR appearing at the output of the receiver 33 can be expressed as:

$$SNR = \frac{V_{EMF}\sqrt{Q^2+1}}{\sqrt{\overline{V^2_{noise,coil}}(Q^2+1) + \overline{V^2_{noise,rec}}}} \tag{S5}$$

Deduced from eqn. (S5), the SNR of the µNMR receiver is a function of Butterfly coil geometry ($V_{EMF}$, $\overline{V^2_{noise,coil}}$ and Q) as well as receiver noise ($\overline{V^2_{noise,rec}}$). With a fixed budget of receiver noise (limited by the semiconductor process and power), the SNR of the µNMR receiver depends on the coil geometry, which necessitated systematic study and optimization involving the finite element analysis simulator and electronic circuit simulations.

Figure 16B:
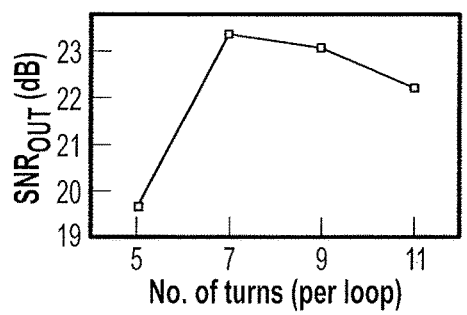
FIG. 16(b) shows the SNR of the μNMR receiver 33 versus the number of turns of the Butterfly coil 18 in this example with a receiver input referred noise of 0.92 nV/√Hz. An optimal number of turns of 7 is obtained by multi-domain simulation.

Butterfly coils with different number of turns (5, 7, 9, 11 turns on each spiral) were studied in COMSOL Multiphysics® including their resistances, inductances, and RF-magnetic field patterns. With simulated receiver noise of 0.92 nV/√Hz, the SNR of distinct Butterfly-coil-input CMOS transceiver are plotted in FIG. 16(b). The derived optimum number of turns for the Butterfly coil is 7 and it is adopted in the µNMR relaxometer of a preferred embodiment of the present invention. Of course, a number of turns for the Butterfly coil other than 7 could be used even if not optimal, including but not limited to 5, 9, and 11. Table S1 summarizes the characteristics of the Butterfly coils:

TABLE S1

Simulated parameters of the Butterfly coil with distinct number of turns per spiral @ 20 MHz.

| Turns | Resistance (Ω) | Inductance (nH) | Q | $\overline{B_1}$ (mT) |
|---|---|---|---|---|
| 5 | 0.795 | 167.4 | 26.5 | 0.292 |
| 7 | 1.486 | 354.8 | 30.0 | 0.596 |
| 9 | 2.61046 | 668.5 | 32.2 | 0.891 |
| 11 | 4.12017 | 1144.4 | 34.9 | 1.190 |

Figure 16C:
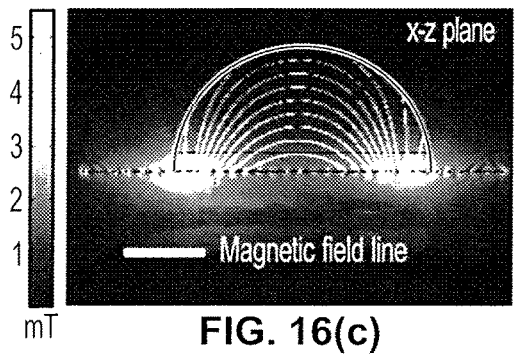
FIG. 16(c) shows the magnetic field pattern of the 7-turn Butterfly coil of an example embodiment in the x-z plane. The RF magnetic field in the center of the Butterfly coil 18 goes in the x-direction.
Figure 16D:
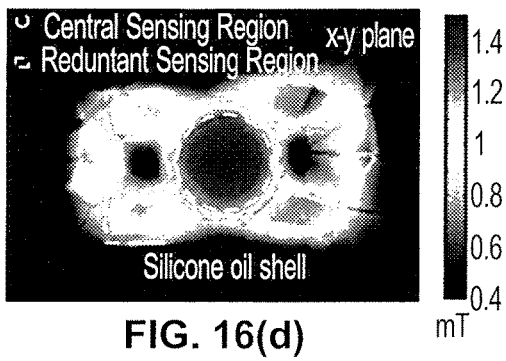
FIG. 16(d) shows the magnetic field pattern of the Butterfly coil in the x-y plane. The center of the Butterfly coil 18 has strongest magnetic field strength with some redundant sensing region.

The magnetic field pattern of the resultant 7-turn Butterfly coil is also demonstrated. The magnetic field in x-z plane and its direction is illustrated in FIG. 16(c). Within the center of the Butterfly coil, the RF magnetic field mainly passes through in x-direction, thus orthogonal to the static magnetic field (z-direction). FIG. 16(d) depicts the magnetic field in the x-y plane. The center region of the Butterfly coil has the strongest magnetic field peaking the µNMR strength, making it suitable for µNMR sensing. Yet, it is surrounded by some redundant sensing regions that may affect the results if they are filled with oil. As explained in the subsequent section, the use of a thin shell of oil applied to each droplet implies that the minimal overlap of the silicone oil with the redundant regions induces negligible effect.

6.5. Digital Microfluidic Module

Figure 17:
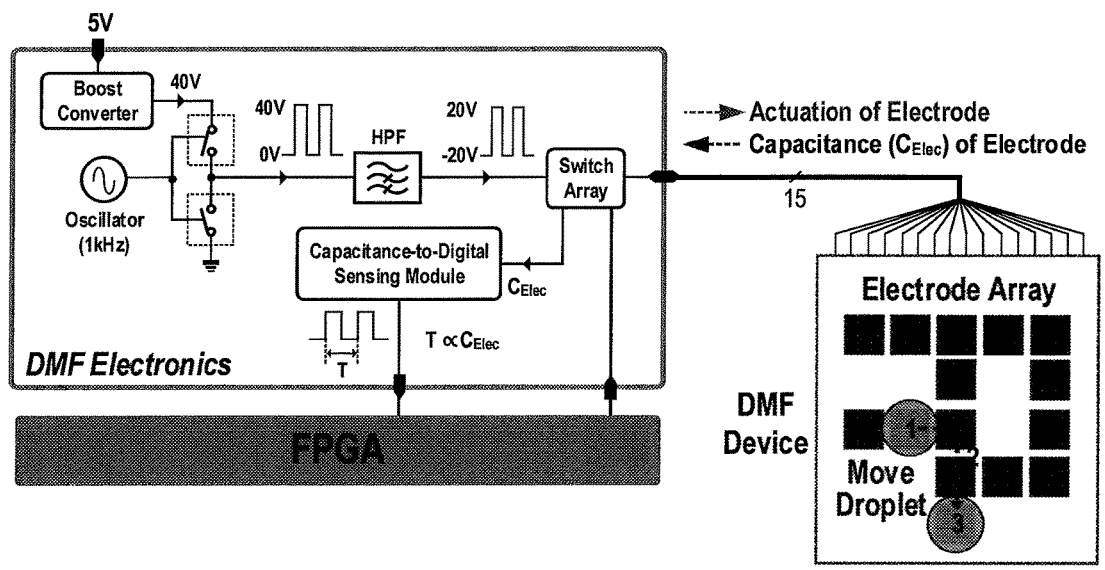
FIG. 17 is a schematic of a DMF module 15 according to an example embodiment of the present invention.

A simplified schematic of the digital microfluidic (DMF) module 15 according to an example embodiment of the invention is shown in FIG. 17. A step-up voltage-to-voltage boost converter 71 was used to built-up with LM3478 switching controller from Texas Instruments Inc. to generate a sufficiently-high voltage signal for electrode actuation. The input power is directly drawn from the FPGA board 20 at 5 V; this act avoids the need of another high-voltage supply for better portability.

An oscillator 73 built up with timer ICM7555 from Intersil (Milpitas, Calif.) is used to generate a square wave of I kHz. This square wave is amplified into a 40-V peak-to-peak voltage by a switch pair 75, and then high-pass filtered by high pass filter 77 to remove the DC level for actuating the electrodes. A switch array 79 mastered by the FPGA 20 was used to control the on-off pattern of the electrodes. To reduce the RMS-voltage stress on the electrode so as to minimize the chance of dielectric breakdown, the driving voltage on an occupied electrode is modulated with on (off) duty cycle of 10% (90%). Exemplified in FIG. 18, after a continuous square wave of 3 s acting on the electrode, the pulse acting on the electrode with droplet is modulated with a turn on-off pattern of 1 to 9. This modulation technique allows the electrode to strap the droplet and prevents the dielectric breakdown of the electrode caused by the long-term voltage stress.

The location of each droplet sample is determined by scanning the derived capacitance $C_{elec}$ of each electrode. As the capacitance between two parallel plates is proportional to the permittivity of its insulating medium, a droplet-occupied electrode will increase the capacitance on the corresponding electrode when compared with the air. In this work, a timer ICM7555 working in the astable mode is used to sense the electrode capacitance. The oscillation frequency of the timer is inversely proportional to the capacitance. Thus, the identification of droplet position can be done by counting the pulses available in a fixed period of time on each electrode.

6.6. DMF Device Fabrication

A fabrication procedure of the DMF device according to an example embodiment of the invention including the top plate and the bottom plate is shown in FIG. 19. As an overview and more specifically, FIG. 19 shows a fabrication procedure of a $Ta_2O_5$/Parylene C-insulated DMF device according to an example embodiment of the invention, in which Steps 1 to 6 show the fabrication process of the plate with electrode, while the fabrication process of the plate with ITO is shown in step 7 to 8. The Assembly of the DMF device together with the Butterfly coil is also shown in the figure. It is noted:

1. The patterns of the electrode array were drawn in AutoCad and the mask with the designed patterns was prepared for lithography on the Cr-coated glass.
2. The patterns were etched on the glass with standard lithography and wet-etch methods.
3. Dielectric layer $Ta_2O_5$ was deposited on the glass by reactive DC magnetron sputtering (HHV, Auto 500) at room temperature with 99.99% Ta target under an $Ar/O_2$ ambient. The chamber pressure was then decompressed to $1.3 \times 10^{-4}$ Pa and back filled with sputtering gas with 15 sccm Ar and 2.05 sccm $O_2$ with power of 110 W and deposition rate of 2.4 nm/min. The thickness of $Ta_2O_5$ layer is 250 nm. In order to suppress the number of pin-holes in the dielectric, the oxidized layer was thermal annealed immediately in N2 atmosphere at 400° C. for 10 mins.
4. Silquest A-174 Silane solution from Momentive Performance Materials Inc. (Columbus Ohio) was adopt to prime the surface of the chip in isopropyl alcohol for 15 mins to strengthen the adhesion between $Ta_2O_5$ and Parylene C coatings, which is coated on the chip later. The glass was then baked at 120° C. for 5 mins.
5. A Parylene-C layer, which is used to screen the pinholes in the $Ta_2O_5$ layer and prevent exposure of $Ta_2O_5$ to liquid samples while maintaining the high dielectric constant and strength of the $Ta_2O_5$, was deposited atop the $Ta_2O_5$ surface by a low pressure chemical vapor deposition method carrying out in LH300 from La-Chi Enterprise Co., Ltd. (Taiwan).
6. Amorphous fluoropolymer hydrophobic layers (100 nm) were formed by spin coating 0.5% Teflon® AF 1601S from Dupont (Wilmington, Del.) in perfluorosilane FC-40 from 3M Co. (St. Paul, Minn.) at 3200 rotation per minute (rpm) for 60 s. Then the glass was treated at 160° C. for 4 hours.
7. ITO coated glass was prepared which functions as a ground node for all the electrodes.
8. Amorphous fluoropolymer hydrophobic layers (100 nm) was formed on the ITO coated glass by spin coating 0.5% Teflon® AF 1601S from Dupont in perfluorosilane FC-40 from 3M Co. at 3200 rpm for 60 s. Then the glass was treated at 160° C. for 4 hours.

The assembly of the resulted DMF device together with the Butterfly coil fabricated on the PCB is shown in FIG. 19.

6.7. Droplet Actuation

Snapshots of a droplet transported from one electrode to its neighbor are shown in FIG. 20(a)-(h). The droplet is at rest first. When a 40-$V_{pp}$ square wave was applied to a neighboring electrode, the droplet moves toward the actuating electrode gradually. The entire movement takes around 3 s, equivalent to an average velocity of 1.17 mm/s.

6.8. µNMR Relaxometer Software and Hardware Interfaces

To facilitate the setting of µNMR parameters and route optimization of DMF, a graphic-user-interface program implemented in Visual C# was adopted to master the whole µNMR relaxometer and includes: i) setting the µNMR parameters; ii) displaying the µNMR results; iii) reading the ambient temperature and calibrating the DAC output; iv) controlling the switch array 79 for the DMF device; and v) displaying the vacancy of the electrodes. To achieve this, an interface is entailed for communications between the FPGA 20 (for hardware control) and the PC 22 (for software computing).

Figure 21:
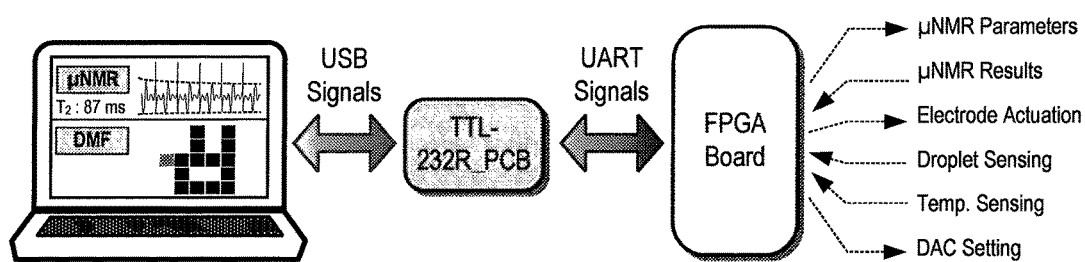
FIG. 21 shows the communication between the PC 22 and the FPGA board 20 in one example embodiment to drive the μNMR relaxometer 10; this is done by adopting the TTL-232R_PCB module 21 to interface between the PC 22 and the FPGA board 20, which mastered the hardware of the μNMR relaxometer 10.

FIG. 21 shows the communication between the PC 22 and the FPGA board 20 to drive the µNMR relaxometer 10 in an example embodiment; this is done by adopting the TTL-232R_PCB module 21 to interface between the PC 22 and the FPGA board 20, which mastered the hardware of the µNMR relaxometer 10. The TTL-232R_PCB module from Future Technology Devices International Limited (United Kingdom) was used for interfacing between the PC 22 and the FPGA board 22. It can read/transmit data from/to FPGA board 20 using UART (universal asynchronous receiver/transmitter) signals, and the PC 22 will process the data from the module. This protocol can ease the design for both hardware and software levels. As shown in FIG. 21, the PC 22 sends data to the FPGA 20 using the TTL-232R_PCB module with a unique address. The module will process the command and convert it to a readable format for the FPGA 20. The FPGA board 20 with a defined address will send the corresponding command to the appropriate module. For instance, if the PC 22 set one of the electrode to the "ON" state for the DMF device, the FPGA 20 will recognize this command and set the corresponding output to a high level, which will set the accompanying switch and drive the electrode for droplet actuation. With the PC 22, all the necessary control of the µNMR relaxometer 10 can be simplified into the software level. This can eliminate the use of cumbersome hardware such as digital logics and switches, providing a neat platform for controlling the µNMR relaxometer 10.

7. Additional Example Implementation(s)

The present invention or various part(s) or function(s) thereof may be implemented using hardware, software, or a combination thereof, and may be implemented in one or more computer systems or other processing systems. A computer system for performing various operations of the present invention and capable of carrying out the functionality described herein can include one or more processors connected to a communications infrastructure (e.g., a communications bus, a cross-over bar, or a network). Various software embodiments are described in terms of such an exemplary computer system. After reading this description, it will become apparent to a person skilled in the relevant art(s) how to implement the invention using other computer systems and/or architectures.

The computer system can include a display interface that forwards graphics, text, and other data from the communication infrastructure (or from a frame buffer) for display on a display unit. The display interface can communicate with a browser. The computer system also includes a main memory, preferably a random access memory, and may also include a secondary memory and a database. The secondary memory may include, for example, a hard disk drive and/or a removable storage drive, representing a floppy disk drive, a magnetic tape drive, an optical disk drive, etc. The removable storage drive reads from and/or writes to a removable storage unit in a well known manner. The removable storage unit can represent a floppy disk, magnetic tape, optical disk, etc. which is read by and written to by the removable storage drive. As will be appreciated, the removable storage unit can include a computer usable storage medium having stored therein computer software and/or data.

The computer system may also include a communications interface which allows software and data to be transferred between the computer system and external devices. The terms "computer program medium" and "computer usable medium" are used to refer generally to media such as the removable storage drive, a hard disk installed in the hard disk drive, and signals. These computer program products provide software to the computer system.

Computer programs or control logic are stored in the main memory and/or the secondary memory. Computer programs may also be received via the communications interface. Such computer programs or control logic (software), when executed, cause the computer system or its processor to perform the features and functions of the present invention, as discussed herein.

8. Conclusion

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. Thus, the present invention should not be limited by any of the above-described exemplary embodiments, but should be defined only in accordance with the following claims and their equivalents.

In addition, it should be understood that the Figures illustrated in the attachments, which highlight the functionality and advantages of the present invention, are presented for example purposes only. The architecture of the present invention is sufficiently flexible and configurable, such that it may be utilized (and navigated) in ways other than that shown in the accompanying figures.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the present invention in any way. It is also to be understood that the steps and processes recited in the claims need not be performed in the order presented.

What is claimed is:

1. A portable μNMR relaxometer system for performing multi-step multi-sample chemical/biological assays, comprising:
  a printed circuit board (PCB) having a CMOS μNMR transceiver, a Butterfly coil, and a Digital Microfluidic (DMF) device integrated thereon; and
  a portable magnet generating a static magnetic field, wherein the portable magnet comprises a housing that surrounds the portable magnet, wherein the housing of the portable magnet comprises an inner gap from one side of the housing to an opposite side of the housing that is configured to at least partially receive the DMF device such that sensing would be performed within the housing of the portable magnet,
  wherein the DMF device comprises a platform of electrodes using electro-wetting-on-dielectric (EWOD) effects, the platform including a sensing site and having top and bottom planes for squeezing a sample, wherein the DMF device is configured to receive one or more samples for analysis at an electrode on the platform and automatically transport the one or more samples on individual paths sequentially to the sensing site, for performing sensing on each sample sequentially,
  wherein the CMOS μNMR transceiver comprises an μNMR circuit that interfaces with the Butterfly coil, the Butterfly coil being disposed on the PCB and directly underneath the DMF device and being at least partially received in the inner gap of the portable magnet, the Butterfly coil generating a surface-parallel RF magnetic field that is parallel to a surface of the PCB and is orthogonal to the static magnetic field generated by the portable magnet for exciting the sample at the μNMR sensing site by transducing a magnetic field produced at the sensing site to an electrical signal which is processed by the CMOS μNMR transceiver to produce an analytical signal.

2. The system of claim 1, wherein the DMF device further comprises a capacitance-to-digital module having a memory and processor configured to automatically determine whether a droplet is located on an electrode of the platform by:
  counting a number of pulses on each electrode;
  comparing the number of pulses counted on each electrode; and
  determining that an electrode having a low number of pulses relative to a high number of pulses at another electrode has a droplet located thereon.

3. The system of claim 1, wherein the platform of the DMF device comprises:
  the top plane, composed of glass and being coated with the electrodes, the electrodes being comprised of Chromium;
  a $Ta_2O_5$ layer underneath the electrodes;
  a Parylene-C layer underneath the $Ta_2O_5$ layer;
  a first Teflon layer under the Parylene-C layer;
  a space for holding the samples which are surrounded on each end by Silicone oil;
  a second Teflon layer underneath the space for holding the samples;
  an ITO layer underneath the second Teflon layer; and
  the bottom plane, composed of glass and disposed underneath the ITO layer.

4. The system of claim 1, further comprising:
  a DMF circuit, configured to control the platform of electrodes of the DMF device;
  a field-programmable gate array (FPGA), configured to transmit commands to the CMOS μNMR transceiver and control the DMF circuit; and
  a signal generator, configured to provide an $LO_{ref}$ signal for input to the CMOS μNMR transceiver.

5. The system of claim 4, wherein the DMF device further comprises a samples actuator comprising:
  an input for receiving input power from the FGPA;
  a boost converter for generating a sufficiently high voltage signal for electrode actuation;
  an oscillator for generating a square wave;
  a switch pair for amplifying the square wave;

a high pass filter (HPF) to high-pass filter the amplified square wave to remove the DC level for actuating the electrodes of the platform; and a switch array controlled by the FGPA to control an on-off pattern of the electrodes by modulating a driving voltage on an occupied electrode with an on-off duty cycle to actuate movement of the sample.

6. The system of claim 1, wherein the DMF device is configured to transport the sample from one electrode on the platform to a neighboring electrode by applying a square wave to the neighboring electrode.

7. The system of claim 1, wherein a Silicone oil shell is applied on the platform of the DMF device to surround the received sample on the platform of electrodes.

8. The system of claim 1, wherein the samples comprise probe-decorated NP droplets and each sample is mixed with a target prior to being transported sequentially and individually to the sensing site.

9. The system of claim 1, wherein the DMF device is configured by a software module such that a first sample is screened at the sensing site while a second sample stays on its electrode, and then after the first sample is guided away from the sensing site the second sample is transported to the sensing site for screening.

10. The system of claim 1, wherein the DMF device is configured by a software module to move a sample onto the sensing site for screening and then away from the sensing site for mixing with a target, and then back to the sensing site for further screening.

11. The system of claim 4, wherein the signal generator comprises:
a temperature sensor to sense an ambient temperature and produce an analog signal relating thereto;
an analog-to-digital converter (ADC) for converting the analog signal to a digital signal;
a processor for reading the digital signal and calculating a working frequency for the $LO_{ref}$ signal;
a digital-to-analog converter for altering the working frequency; and
a voltage-controller oscillator to produce the $LO_{ref}$ signal from the working frequency and output the $LO_{ref}$ signal.

12. The system of claim 4, wherein the CMOS μNMR transceiver further comprises:
a transmitter adapted to power the Butterfly coil, comprising:
a state control and pulse sequence synthesizer to receive the $LO_{ref}$ signal from the signal generator and read the commands transmitted from the FGPA, and
a power amplifier configured to generate CPMG pulse sequences and excite the nuclei of the sample at the sensing site with the CPMG pulses via the Butterfly coil; and
a receiver adapted to extract the μNMR signal induced by the Butterfly coil from the protons, comprising:
a multi-stage low-noise amplifier (LNA) at a front of the receiver to boost the gain and enhance the signal-to-noise ratio (SNR) of the RF signal,
a pair of quadrature mixers configured to downconvert the RF signal to an intermediate frequency (IF) signal for filtering and digitalization, and
a dynamic-bandwidth lowpass filter (LPF) configured to process the IF signal to suppress out-of-band noise and high frequencies generated by the mixers.

13. The system of claim 12, wherein the LPF is a $6^{th}$-order Butterworth filter using source-follower-based topology.

14. The system of claim 5, further comprising a portable computer, configured to:
set μNMR parameters, sample routing, and positioning, display μNMR results,
read ambient temperature,
control the switch array of the DMF device,
display vacancy of the electrodes on the platform, and
display results of the micro-NMR sensing in real time.

15. The system of claim 1, further comprising a pipette configured to receive a sample for analysis and deliver the sample to the DMF device.

16. The system of claim 1, wherein the transceiver comprises multiple receivers which interface with multiple Butterfly coils, each receiver interfacing with a respective Butterfly coil disposed inside the opening gap of the portable magnet.

17. The system of claim 1, wherein the Butterfly coil comprises 7 turns.

18. A method for performing multi-step multi-sample chemical/biological assays using a portable μNMR relaxometer system which comprises a printed circuit board (PCB) having a CMOS μNMR transceiver and a Digital Microfluidic (DMF) device integrated thereon, and a portable magnet generating a static magnetic field, wherein the portable magnet comprises a housing that surrounds the portable magnet, wherein the housing of the portable magnet within a body of the portable magnet comprises an inner gap from one side of the housing to an opposite side of the housing that is configured to at least partially receive the DMF device such that sensing would be performed within the housing of the portable magnet, wherein the DMF device comprises a platform of electrodes using electro-wetting-on-dielectric (EWOD) effects, the platform including a sensing site and having top and bottom planes for squeezing a sample, the method comprising:
receiving one or more samples for analysis at an electrode on the platform;
automatically transporting the one or more samples on individual paths of the platform sequentially to the sensing site, for performing sensing on each sample sequentially;
interfacing with a Butterfly coil disposed on the PCB and directly underneath the DMF device and being at least partially received in the inner gap of the portable magnet, the Butterfly coil generating a surface-parallel RF magnetic field that is parallel to a surface of the PCB and is orthogonal to the static magnetic field generated by the portable magnet for exciting the sample at the μNMR sensing site by transducing a magnetic field produced at the sensing site to an electrical signal; and
processing the electrical signal by the CMOS μNMR transceiver to produce an analytical signal.

19. The method of claim 18, further comprising automatically determining whether a droplet is located on an electrode of the platform by:
counting a number of pulses on each electrode;
comparing the number of pulses counted on each electrode; and
determining that an electrode having a low number of pulses relative to a high number of pulses at another electrode has a droplet located thereon.

20. The method of claim 18, further comprising applying Silicone oil on the platform of the DMF device to surround the received sample on the platform of electrodes.

21. The method of claim 18, wherein the samples comprise probe-decorated NP droplets and further comprising mixing each sample with a target prior to being transported sequentially and individually to the sensing site.

22. A non-transitory computer-readable medium storing a program which, when executed by at least one processor, performs a method for performing multi-step multi-sample chemical/biological assays using the system of claim 1, the method comprising:
controlling the DMF device to automatically transport one or more samples received at an electrode on the platform, on individual paths of the platform sequentially to the sensing site, for performing sensing on each sample sequentially.

23. The non-transitory computer-readable medium of claim 22, wherein the program controls the DMF device to automatically determine whether a droplet is located on an electrode of the platform by:
counting a number of pulses on each electrode;
comparing the number of pulses counted on each electrode; and
determining that an electrode having a low number of pulses relative to a high number of pulses at another electrode has a droplet located thereon.

24. A method for performing multi-step multi-sample chemical/biological assays, the method comprising:
providing the portable μNMR relaxometer system of claim 1;
providing a first droplet and a second droplet on a first electrode and a second electrode, respectively;
providing a first target and a second target on a third electrode and a fourth electrode, respectively;
mixing the first droplet with the first target to form a first mixture and the second droplet with the second target to form a second mixture by transporting the first droplet to the third electrode and the second droplet to the fourth electrode, respectively;
transporting the first mixture to the sensing site for sensing on a first path while the second mixture stays on its electrode;
transporting the first mixture away from the sensing site; and
transporting the second mixture to the sensing site for sensing on a second path while the first mixture stays on its electrode.

25. A method for performing multi-step multi-sample chemical/biological assays, the method comprising:
providing the portable μNMR relaxometer system of claim 1;
providing a droplet on a first electrode;
providing a first target and a second target on a second electrode and a third electrode, respectively;
transporting the droplet to the sensing site for recording a spin-spin relaxation time as a reference;
mixing the droplet with the first target to form a first mixture by transporting the first droplet to the second electrode;
transporting the first mixture to the sensing site for sensing;
transporting the first mixture to the third electrode to form a second mixture by transporting the first mixture to the third electrode; and
transporting the second mixture to the sensing site for sensing.

* * * * *